US012569270B2

(12) United States Patent
Gonenc et al.

(10) Patent No.: US 12,569,270 B2
(45) Date of Patent: Mar. 10, 2026

(54) METHOD AND SYSTEM FOR ESTIMATING TEMPERATURE OF AN END EFFECTOR OF AN ULTRASONIC INSTRUMENT

(71) Applicant: Verb Surgical Inc., Santa Clara, CA (US)

(72) Inventors: Berk Gonenc, San Jose, CA (US); Nikhil Murty, San Francisco, CA (US)

(73) Assignee: AURIS HEALTH, INC., Santa Clara, CA (US)

( * ) Notice: Subject to any disclaimer, the term of this patent is extended or adjusted under 35 U.S.C. 154(b) by 280 days.

(21) Appl. No.: 18/190,015

(22) Filed: Mar. 24, 2023

(65) Prior Publication Data

US 2024/0315723 A1 Sep. 26, 2024

(51) Int. Cl.

*A61B 17/32* (2006.01)
*A61B 18/14* (2006.01)
*A61B 17/00* (2006.01)

(52) U.S. Cl.

CPC .. *A61B 17/320068* (2013.01); *A61B 18/1442* (2013.01); *A61B 2017/00026* (2013.01)

(58) Field of Classification Search

CPC ........ A61B 17/320068; A61B 18/1442; A61B 2017/00026; A61B 2017/00084; A61B 17/320092

See application file for complete search history.

(56) References Cited

U.S. PATENT DOCUMENTS

| | | | | |
|---|---|---|---|---|
| 10,677,764 | B2 * | 6/2020 | Ross | G01N 29/44 |
| 10,955,387 | B2 | 3/2021 | Ross et al. | |
| 11,589,888 | B2 * | 2/2023 | Shelton, IV | G16H 70/20 |
| 12,343,033 | B2 * | 7/2025 | Farvardin | A61B 17/320016 |
| 12,369,938 | B2 * | 7/2025 | Gonenc | A61B 17/320016 |
| 2003/0105480 | A1 | 6/2003 | Wiener et al. | |
| 2010/0036405 | A1 | 2/2010 | Giordano et al. | |
| 2011/0082486 | A1 | 4/2011 | Messerly et al. | |
| 2013/0030561 | A1 | 1/2013 | Imanari | |
| 2020/0030021 | A1 | 1/2020 | Yates et al. | |

FOREIGN PATENT DOCUMENTS

WO 2011/084957 A1 7/2011

OTHER PUBLICATIONS

International Search Report and Written Opinion of the International Searching Authority issued for PCT Patent Application No. PCT/IB2024/051714, mailed on May 20, 2024, 9 pages.

* cited by examiner

*Primary Examiner* — Julian W Woo
(74) *Attorney, Agent, or Firm* — Aikin & Gallant, LLP

(57) ABSTRACT

A method performed by a surgical system. The method determines a resonance frequency of an end effector of an ultrasonic instrument, and determines whether the end effector of the ultrasonic instrument is in a heating state or a cooling state. Responsive to determining that the end effector is in the heating state, the method estimates a temperature of the end effector based on output of a first temperature model that has input based on the resonance frequency. Responsive, however, to determining that the end effector is in the cooling state, the method estimates the temperature of the end effector based on output of a second temperature model that has input based on the resonance frequency. The method presents a notification based on the estimated temperature.

20 Claims, 10 Drawing Sheets

Process
70

61 — Determine a starting temperature of the end effector of the ultrasonic instrument 71 — Determine a cooling start resonance frequency of the end effector of the ultrasonic instrument 63 — Determine a resonance frequency of the end effector 72 — Determine an impedance of the end effector 73 — Determine a corrected resonance frequency based on the impedance and the resonance frequency 74 — Determine a change in the cooling start resonance frequency based on the corrected resonance frequency 75 — Is the end effector in contact with an object?

79 — Determine model coefficients for an air-cooling temperature model

76 — Determine model coefficients for a contact-cooling temperature model

81 — Determine a change in temperature using the air-cooling temperature model based on the (change in the) cooling start resonance frequency and the model coefficients 77 — Determine a change in temperature using the contact-cooling temperature model based on the (change in the) cooling start resonance frequency and the model coefficients 78 — Determine the temperature of the end effector based on the starting temperature and the change in temperature.

67 — Present a notification based on the temperature of the end effector

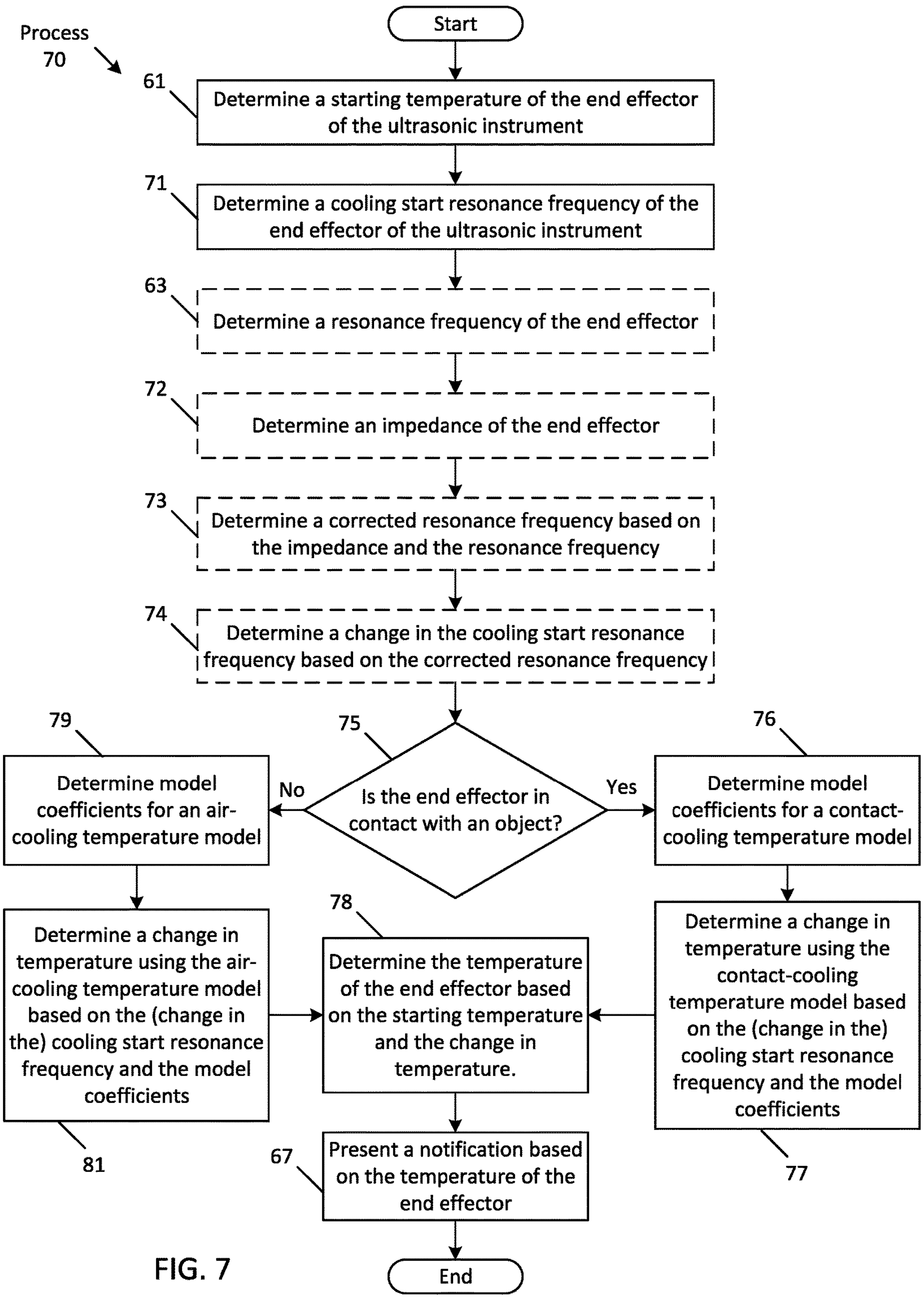

FIG. 7

Process 80

81 Determine a baseline resonance frequency of the end effector of the ultrasonic instrument 82 Determine a baseline temperature of the end effector 61 Determine a starting temperature of the end effector of the ultrasonic instrument 71 Determine a cooling start resonance frequency of the end effector of the ultrasonic instrument 63 Determine a resonance frequency of the end effector 72 Determine an impedance of the end effector 73 Determine a corrected resonance frequency based on the impedance and the resonance frequency 75 Is the end effector in contact with an object?

85 Determine model coefficients for an air-cooling temperature model based on the starting temperature, the cooling start resonance frequency, the baseline resonance frequency, and/or the baseline temperature 83 Determine model coefficients for a contact-cooling temperature model based on the starting temperature, the cooling start resonance frequency, the baseline resonance frequency, and/or the baseline temperature 86 Determine a temperature using the air-cooling temperature model based on the (corrected) resonance frequency and the model coefficients 84 Determine a temperature using the contact-cooling temperature model based on the (corrected) resonance frequency and the model coefficients 67 Present a notification based on the temperature of the end effector Start End

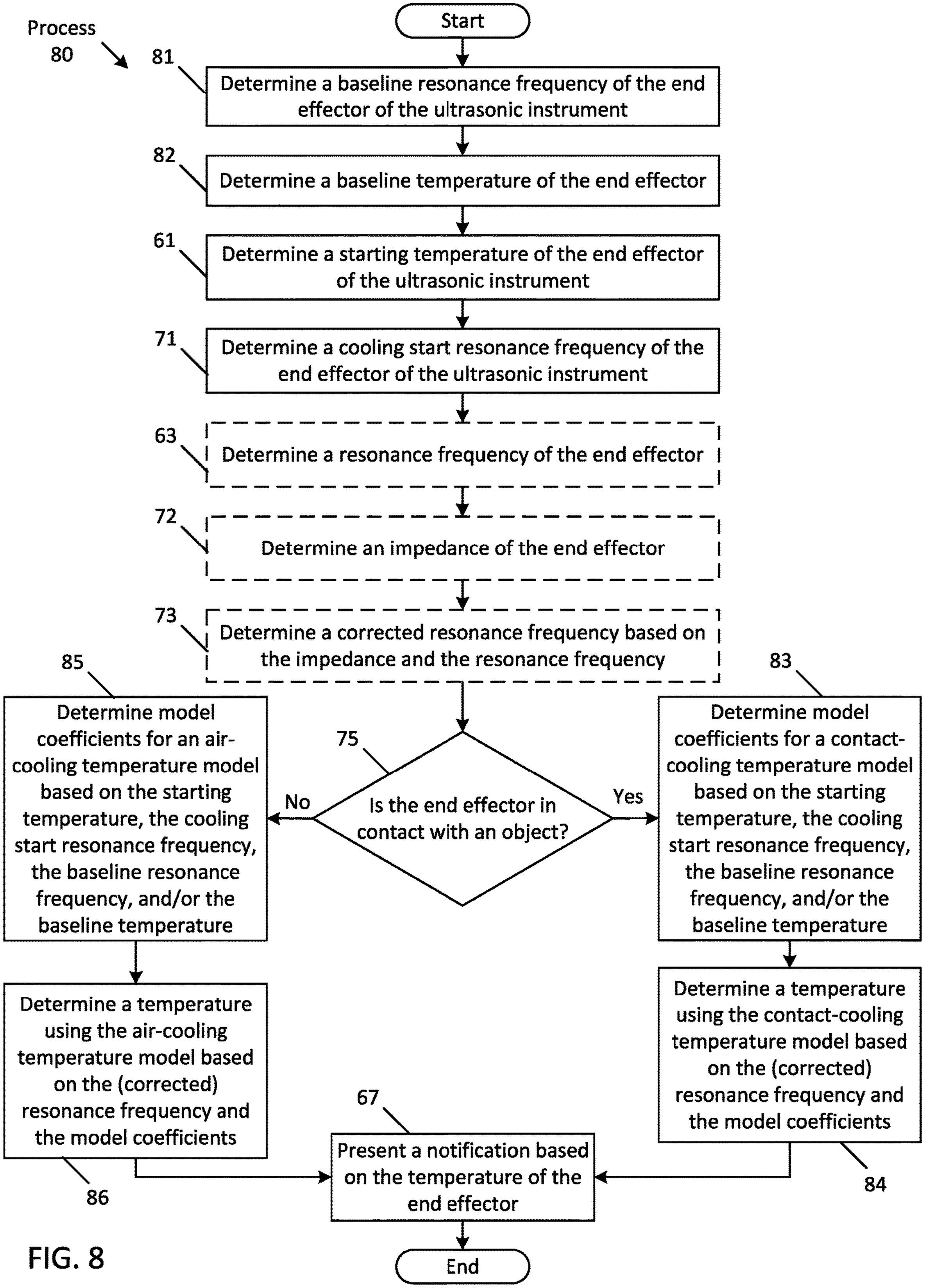

FIG. 8

METHOD AND SYSTEM FOR ESTIMATING TEMPERATURE OF AN END EFFECTOR OF AN ULTRASONIC INSTRUMENT

FIELD

Various embodiments of the disclosure relate generally to surgical systems, and more specifically to a surgical system for estimating temperature of an end effector of an ultrasonic instrument. Other embodiments are also described.

BACKGROUND

Minimally-invasive surgery, MIS, such as laparoscopic surgery, uses techniques that are intended to reduce tissue damage during a surgical procedure. Laparoscopic procedures typically call for creating a number of small incisions in the patient, e.g., in the abdomen, through which several surgical tools such as an endoscope, a blade, a grasper, and a needle, are then inserted into the patient. A gas is injected into the abdomen which insufflates the abdomen thereby providing more space around the tips of the tools, making it easier for the surgeon to see (via the endoscope) and manipulate tissue at the surgical site. MIS can be performed faster and with less surgeon fatigue using a surgical robotic system in which the surgical tools are operatively attached to the distal ends of robotic arms, and a control system actuates the arm and its attached tool. The tip of the tool will mimic the position and orientation movements of a handheld user input device (UID) as the latter is being manipulated by the surgeon. The surgical robotic system may have multiple surgical arms, one or more of which has an attached endoscope and others have attached surgical instruments for performing certain surgical actions.

Control inputs from a user (e.g., surgeon or other operator) are captured via one or more user input devices and then translated into control of the robotic system. For example, in response to user commands, a tool drive having one or more motors may actuate one or more degrees of freedom of a surgical tool when the surgical tool is positioned at the surgical site in the patient.

SUMMARY

A surgical tool that is used in some MIS procedures is an ultrasonic instrument that uses ultrasonic vibration at its tip to rapidly generate heat for cutting and cauterizing tissue. The tip may include a blade that reaches high temperatures (e.g., greater than 300° C.) during a "heating" cycle (or state) in which the blade oscillates against a piece of tissue, thereby producing heat due to friction between the blade and the tissue during the oscillation. In particular, the system may activate the instrument, causing the blade to enter the heating cycle, in response to receiving user input by an operator, such as when the user presses on a petal or a button. After reaching a high temperature, the blade may be used to dissect a portion of tissue, while also sealing the remaining tissue. By performing multiple tasks (e.g., cutting for dissection, cauterizing, etc.), the use of the tool during a laparoscopic surgery reduces instrument exchanges and the number of instruments during the procedure.

After using the ultrasonic instrument in its heated state, the operator may cease providing user input (e.g., releasing the petal or the button), thereby deactivating the instrument and allowing the blade to cool. During this time, however, the rate at which the blade cools remains unknown to the operator. As a result, the blade may remain at a high temperature (e.g., greater than a threshold temperature), which may be too hot to come into contact with an object, such as human tissue, for a period of time as the blade cools. In addition, this period of time may vary (e.g., being as long as at least thirty seconds) based on the blade's last temperature while the instrument is in the heating cycle. This causes inefficiency while the instrument is in use, and without being able to monitor the blade's temperature between cycles, conventional systems are unable to actively control an ultrasonic instrument to maintain a blade's temperature at or below a desired temperature.

The present disclose provides a laparoscopic surgical system that efficiently estimates a temperature of an ultrasonic instrument during (and between) a blade's heating cycle and a cooling cycle, using different temperature models. Specifically, the system may activate the instrument into a heating cycle by providing power (e.g., in response to receiving user input by an operator, such as pressing on a petal or button) for the instrument's blade to oscillate, as it is used to dissect tissue. While the instrument is active in this "high-power" state, the system may determine the temperature of the blade based on one or more characteristics (e.g., an input voltage, an input current, a resonance frequency, etc.) of the instrument using a heating temperature model. After the heating cycle is terminated (e.g., the operator releasing the petal), the system may enter a "low-power" state (or cooling cycle) in which the ultrasonic instrument may draw less power (e.g., to be provided less current) to cause the blade to vibrate less than while the instrument is in the high-power state. While in this low-power state, the instrument may not draw sufficient power to produce frictional heat (e.g., due to the blade vibrating over a lower excursion than needed to produce the heat), but may have sufficient power to determine one or more characteristics of the instrument, such as a resonance frequency of the blade with which the system may use to estimate the temperature of the ultrasonic instrument using a cooling temperature model. As a result, the system may provide the operator with a (e.g., continuous) temperature reading based on temperature estimated using different models as the ultrasonic instrument transitions between heating and cooling cycles.

The present disclosure provides a surgical system that estimates a temperature of an end effector, e.g., for display to an operator, while the end effector is in use by the operator. Specifically, the system determines one or more characteristics of the end effector, such as a resonance frequency of the end effector, and determines whether the end effector is in the heating state or the cooling state. For instance, the resonance frequency may be a frequency at which the (e.g., blade of the) end effector vibrates at (or as) the end effector enters the heating state or the cooling state. Responsive to determining that the end effector is in the heating state, the system may estimate a temperature of the end effector based on output of a first (or heating) temperature model that has input based on the resonance frequency. Responsive, however, to determining that the end effector is in the cooling state, the system may estimate the temperature of the end effector based on output of a second (or cooling) temperature model that has input based on the resonance frequency. The system may present a notification based on the estimated temperature. For example, the system may display a pop-up notification on a display that includes the estimated temperature. As a result, the system is able to estimate the temperature of the end effector between different states (e.g., as the operator uses the end effector during a surgical procedure) in a cohesive and efficient manner.

In one embodiment, the resonance frequency is a first resonance frequency that is at a starting time at which the end effector enters the heating state or the cooling state, where the system determines a starting temperature of the end effector at the starting time; and determines a second resonance frequency of the end effector of the ultrasonic instrument at a time that is subsequent to the starting time. In another embodiment, the temperature is estimated based on the starting temperature, the first resonance frequency, and the second resonance frequency. In some embodiments, estimating the temperature, responsive to determining that the end effector is in the heating state, includes determining a change in temperature of the end effector based on a difference between the first resonance frequency and the second resonance frequency; and combining the change in temperature and the starting temperature.

In one embodiment, estimating the temperature, responsive to determining that the end effector is in the cooling state, includes: determining whether the end effector is being air-cooled or is being contact-cooled; responsive to determining that the end effector is being air-cooled, estimating the temperature of the end effector based on output of a first cooling temperature model; and responsive to determining that the end effector is being contact-cooled, estimating the temperature of the end effector based on output of a second cooling temperature model. In another embodiment, the first cooling temperature model is a polynomial model, and the second cooling temperature model is an exponential model.

In one embodiment, the resonance frequency is a first resonance frequency, where estimating the temperature of the end effector based on output of the second temperature model includes: determining model coefficients for the second temperature model based on the first resonance frequency; determining a second resonance frequency of the end effector of the ultrasonic instrument; and determining the temperature by applying input into the second temperature model based on the second resonance frequency and the model coefficients. In another embodiment, the system determines an impedance of the end effector based on input current of the ultrasonic instrument; and determines a corrected resonance frequency based on the impedance and the second resonance frequency. In some embodiments, determining the temperature of the end effector based on output of the second temperature model includes applying the corrected resonance frequency as input into the second temperature model.

In one embodiment, the system determines an input current that is being provided to the ultrasonic instrument, where determining whether the end effector is in a heating state or a cooling state includes: determining that the end effector is in the heating state when the input current is greater than (or equal to) the current threshold; and determining that the end effector is in the cooling state when the input current is less than the current threshold. In another embodiment, the system determines an impedance of the end effector based on the input current; responsive to determining that the impedance is greater than a threshold, determines that the end effector is in the cooling state while in-air; and responsive to determining that the impedance is less than the threshold, determines that the end effector is in the cooling state while in contact with an object.

The above summary does not include an exhaustive list of all embodiments of the disclosure. It is contemplated that the disclosure includes all systems and methods that can be practiced from all suitable combinations of the various embodiments summarized above, as well as those disclosed in the Detailed Description below and particularly pointed out in the claims. Such combinations may have particular advantages not specifically recited in the above summary.

BRIEF DESCRIPTION OF THE DRAWINGS

The embodiments are illustrated by way of example and not by way of limitation in the figures of the accompanying drawings in which like references indicate similar elements. It should be noted that references to "an" or "one" embodiment of this disclosure are not necessarily to the same embodiment, and they mean at least one. Also, in the interest of conciseness and reducing the total number of figures, a given figure may be used to illustrate the features of more than one embodiment, and not all elements in the figure may be required for a given embodiment.

FIG. 7 is a flowchart of one embodiment of a process for estimating a temperature of an end effector of an ultrasonic instrument while the end effector is in a cooling state.

FIG. 8 is a flowchart of another embodiment of a process for estimating a temperature of an end effector of an ultrasonic instrument while the end effector is in a cooling state.

DETAILED DESCRIPTION

Several embodiments of the disclosure with reference to the appended drawings are now explained. Whenever the shapes, relative positions and other embodiments of the parts described in a given embodiment are not explicitly defined, the scope of the disclosure here is not limited only to the parts shown, which are meant merely for the purpose of illustration. Also, while numerous details are set forth, it is understood that some embodiments may be practiced without these details. In other instances, well-known circuits, structures, and techniques have not been shown in detail so as not to obscure the understanding of this description. Furthermore, unless the meaning is clearly to the contrary, all ranges set forth herein are deemed to be inclusive of each range's endpoints.

Figure 1:
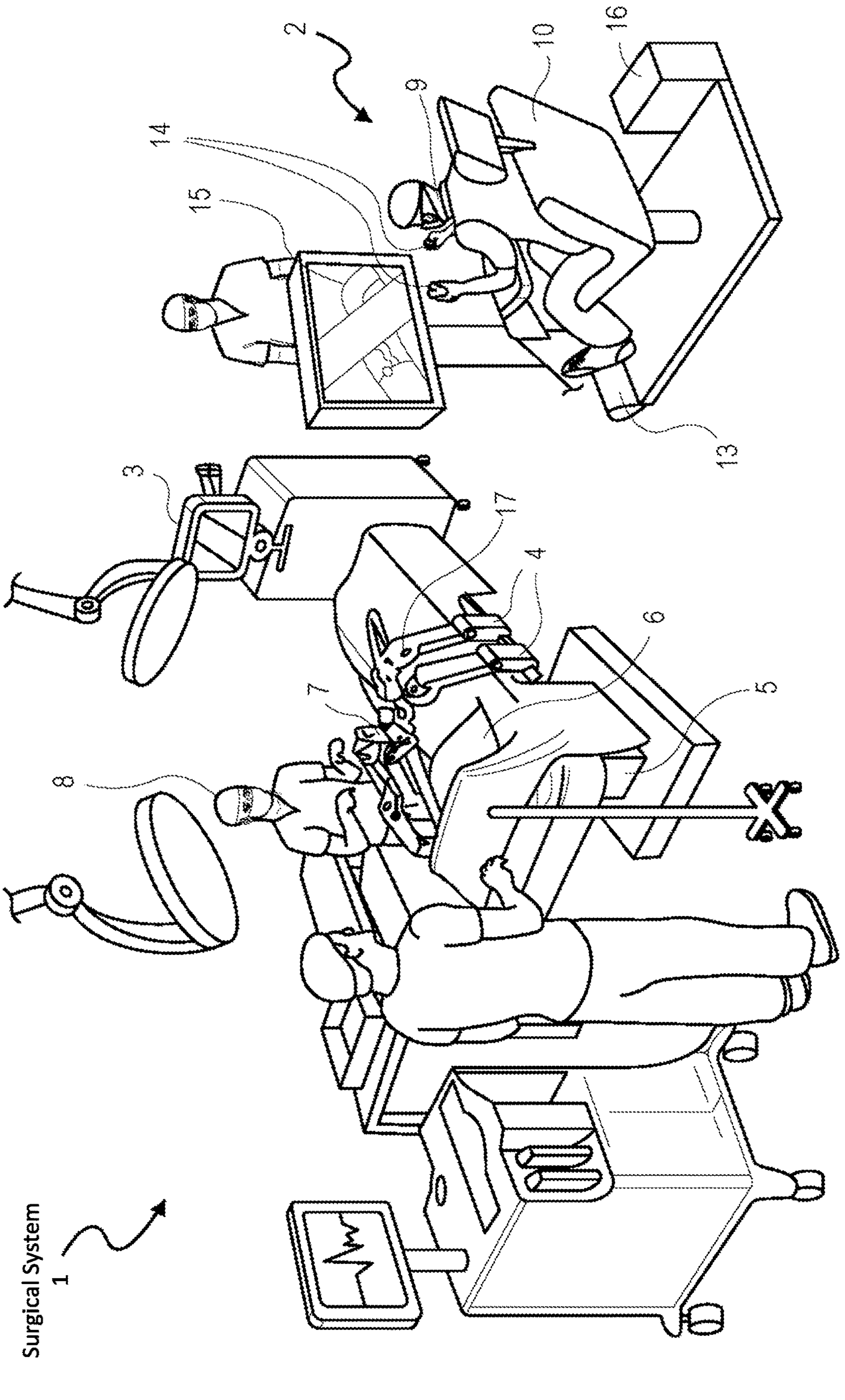
FIG. 1 shows a pictorial view of an example surgical system in an operating arena.

FIG. 1 shows a pictorial view of an example (e.g., laparoscopic) surgical system (which hereafter may be referred to as "system") 1 in an operating arena. The system 1 includes a user console 2, a control tower 3, and one or more surgical robotic arms 4 at a surgical robotic table (surgical table or surgical platform) 5. In one embodiment, the arms 4 may be mounted to a table or bed on which the patient rests as shown in the example of FIG. 1. In one embodiment, at least some of the arms 4 may be configured differently. For example, at least some of the arms may be mounted on a ceiling, sidewall, or in another suitable structural support, such as a cart separate from the table. The system 1 can incorporate any number of devices, tools, or accessories used to perform surgery on a patient 6. For example, the system 1 may include one or more surgical tools (instruments) 7 used to perform surgery (surgical procedure). A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. For example, when manually controlled an operator may (e.g., physically) hold a portion of the tool (e.g., a handle), and may manually control the tool by moving the handle and/or pressing one or more input controls (e.g., buttons) on the (e.g., handle of the) tool. In another embodiment, when controlled robotically, the surgical system may manipulate the surgical tool based user input (e.g., received via the user console 2, as described herein).

Generally, a remote operator 9, such as a surgeon or other operator, may use the user console 2 to remotely manipulate the arms 4 and/or the attached surgical tools 7, e.g., during a teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may include one or more components, such as a seat 10, one or more foot-operated controls (or foot pedals) 13, one or more (handheld) user-input devices (UIDs) 14, and at least one display 15. The display is configured to display, for example, a view of the surgical site inside the patient 6. The display may be configured to display image data (e.g., still images and/or video). In one embodiment, the display may be any type of display, such as a liquid crystal display (LCD), a light-emitting diode (LED) display, an organic LED (OLED) display, etc. In some embodiments, the display may be a 3D immersive display that is for displaying 3D (surgical) presentations. For instance, during a surgical procedure one or more endoscopic cameras may be capturing image data of a surgical site, which the display presents to the user in 3D. In one embodiment, the 3D display may be an autostereoscopic display that provides 3D perception to the user without the need for special glasses. As another example, the 3D display may be a stereoscopic display that provides 3D perception with the use of glasses (e.g., via active shutter or polarized).

In another embodiment, the display 15 may be configured to display at last one graphical user interface (GUI) that may provide informative and/or interactive content, to thereby assist a user in performing a surgical procedure with one or more instruments in the surgical system 1. For example, some of the content displayed may include image data captured by one or more endoscopic cameras, as described herein. In another embodiment, the GUI may include selectable UI items, which when manipulated by the user may cause the system to perform one or more operations. For instance, the GUI may include a UI item as interactive content to switch control between robotic arms. In one embodiment, to interact with the GUI, the system may include input devices, such as a keyboard, a mouse, etc. In another embodiment, the user may interact with the GUI using the UID 14. For instance, the user may manipulate the UID to navigate through the GUI, (e.g., with a cursor), and to make a selection may hover the cursor over a UI item and manipulate the UID (e.g., selecting a control or button). In some embodiments, the display may be a touch-sensitive display screen. In this case, the user may perform a selection by navigating and selecting through touching the display. In some embodiments, any method may be used to navigate and/or select a UI item.

As shown, the remote operator 9 is sitting in the seat 10 and viewing the user display 15 while manipulating a foot-operated control 13 and a handheld UID 14 in order to remotely control one or more of the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the system 1 are in a stowed configuration or withdrawn configuration (to facilitate access to the surgical site.) Once access is completed, initial positioning or preparation of the system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to drive (move) one or more robotic arm actuators 17 (or driving mechanism) in the system 1 for teleoperation. The UID 14 may be communicatively coupled to the rest of the system 1, e.g., via a console computer system 16 (or host). The UID 14 can generate spatial state signals corresponding to movement of the UID 14, e.g. position and orientation of the handheld housing of the UID, and the spatial state signals may be input signals to control motions of the robotic arm actuators 17. The system 1 may use control signals derived from the spatial state signals, to control proportional motion of the actuators 17. In one embodiment, a console processor of the console computer system 16 receives the spatial state signals and generates the corresponding control signals. Based on these control signals, which control how the actuators 17 are energized to drive a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn drives other linkages, gears, etc., of the system 1. The system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator that opens or closes jaws of the grasper at a distal end of surgical tool 7 to grip tissue within patient 6.

In some embodiments, the communication between the surgical robotic table 5 and the user console 2 may be through a control tower 3, which may translate user commands that are received from the user console 2 (and more particularly from the console computer system 16) into robotic control commands that transmitted to the arms 4 on the surgical table 5. The control tower 3 may also transmit status and feedback from the surgical table 5 back to the user console 2. The communication connections between the surgical table 5, the user console 2, and the control tower 3 may be via wired (e.g., optical fiber) and/or wireless links, using any suitable one of a variety of wireless data communication protocols, such as BLUETOOTH protocol. Any wired connections may be optionally built into the floor and/or walls or ceiling of the operating room. The system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
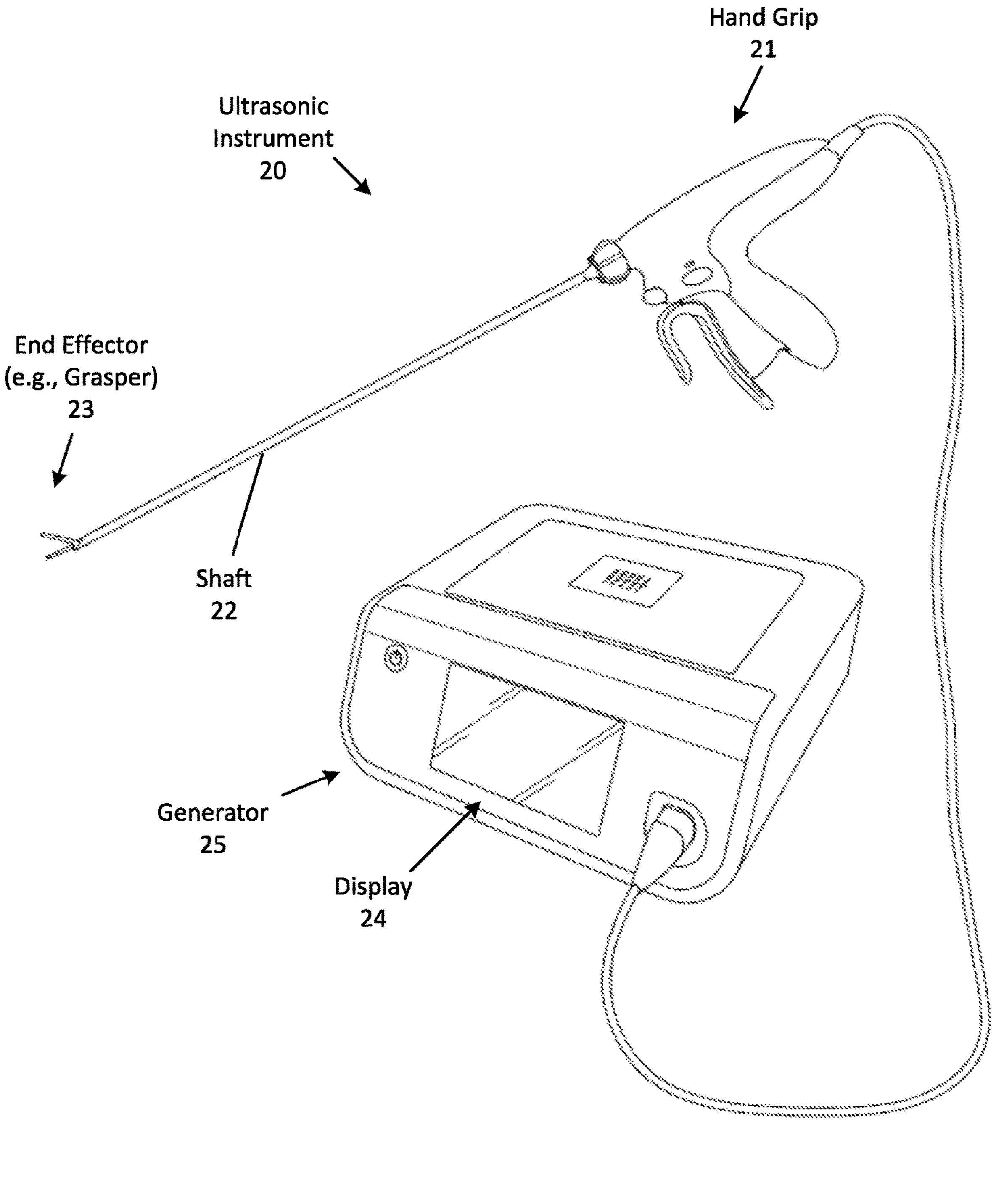
FIG. 2 shows a pictorial view of an ultrasonic instrument and a generator according to one embodiment of the disclosure.

FIG. 2 shows a pictorial view of an ultrasonic instrument 20 and a generator 25 according to one embodiment of the disclosure. As shown, the ultrasonic instrument may be a hand-held laparoscopic tool that is configured to perform ultrasonic surgical operations or task, such as cutting, sealing (cauterizing) tissue, etc., based on manual operations/manipulations (e.g., of a hand grip 21) of the instrument by an operator (e.g., surgeon). For instance, during a laparoscopic (or endoscopic) surgical procedure, a small incision may be made in a patient to create an opening (or port), and the ultrasonic instrument may be inserted, via the opening, into a cavity of the patient (e.g., a gas is used for insufflation of the cavity), where the end effector may be used by the operator to manipulate tissue and perform surgical operations (e.g., cutting and/or cauterizing, etc.). The ultrasonic instrument is coupled (e.g., via a cable) to the generator (as shown) that enables the ultrasonic instrument to operate in one or more power states, as described herein.

The ultrasonic instrument includes the hand grip (e.g., which includes a tool drive) 21, a shaft (or cannula) 22, and an end effector 23 (e.g., which may be coupled to a shaft of the instrument) that may be loaded into the cannula, in accordance with embodiments of the subject technology.

The hand grip 21 may be arranged to be held by an operator, and may allow the operator to manipulate the (e.g., end effector 23 of the) ultrasonic instrument during a surgical operation. In one embodiment, the hand grip may include one or more inputs (e.g., a trigger, one or more buttons, etc.), that allow an operator to control the ultrasonic instrument. For example, the instrument may include a trigger, which when pulled by one or more fingers of the user while being held produces a control signal that allows the user to control the end effector of the instrument (and/or control a portion of the surgical system). In particular, the trigger may be arranged to manipulate the end effector (e.g., by adjusting the position of the hinged arm 31 shown in FIG. 3). In another embodiment, the hand grip may include one or more inputs for changing a power state of the instrument. More about power states of the instrument are described herein.

As described herein, the hand grip may include a tool drive (not shown) that may be arranged to drive the end effector 23 of the ultrasonic instrument. Specifically, the tool drive may include a (e.g., linear) motor or actuator that may be arranged to vibrate (or oscillate) the (e.g., blade of the) end effector at one or more frequencies (e.g., at a very high (ultrasonic) frequency, and/or at a low frequency). In some embodiments, the tool drive is configured to vibrate the end effector such that a portion of the end effector (e.g., a blade) moves back and forth along one or more axes. Specifically, the tool drive may vibrate the end effector over one or more excursions, where over each excursion the (e.g., blade of the) end effector may be displaced at a (e.g., different) distance from a starting (or beginning) position. More about how the end effector vibrates is described herein. In another embodiment, the tool drive may include an ultrasonic transducer that is configured to vibrate the end effector according to an input voltage/input current (e.g., applied by the generator 25).

As described thus far, the ultrasonic instrument may include the end effector 23 and the hand grip 21 (which may include a tool drive). Specifically, the instrument includes the grip 21, the shaft 22 that is coupled to a distal end of the hand grip, and the end effector 23 that may be coupled to a distal end of the shaft. In which case, the ultrasonic instrument as referred herein may be the end effector, which may be coupled to the (e.g., tool drive via the shaft 22 of the) hand grip. In one embodiment, the (e.g., end effector of the) ultrasonic instrument may be separate from (and removably coupled to) the hand grip. In some embodiments, the shaft receives and guides (e.g., a shaft of) the blade in order to couple to the instrument.

As described herein, the surgical system 1 includes the ultrasonic instrument 20 that is configured to produce heat based on vibrations of its end effector 23. In another embodiment, the instrument may be any type of energy (e.g., endoscopic, laparoscopic, etc.) tool that is designed to generate heat.

As described thus far, the ultrasonic instrument 20 may be a hand-held laparoscopic instrument that may be manually is held and manipulated by an operator. In another embodiment, the instrument may be a part of a surgical robotic arm. Specifically, the ultrasonic instrument may be coupled to a robotic arm and powered by the generator, as described herein. For example, the ultrasonic instrument may be coupled to a distal end of a robotic arm (e.g., arm 4 in FIG. 1), which includes several components that allow the robotic arm to be controlled by an operator. For example, the surgical robotic arm 4 may include a plurality of links and a plurality of actuated joint modules for actuating the plurality of links relative to one another. The joint modules may include various types, such as a pitch joint or a roll joint, which may substantially constrain the movement of the adjacent links around certain axes relative to others. The plurality of the joint modules of the robotic arm 4 can be actuated to position and orient the ultrasonic instrument for robotic surgeries. In one embodiment, the ultrasonic instrument may be coupled to the distal end via a tool drive that is arranged to actuate the end effector 23 of the instrument.

In the case in which the ultrasonic instrument is coupled to a robotic arm, movement and operation of the ultrasonic instrument may be performed via one or more user controls (e.g., UIDs, foot pedals, etc.) that are coupled to the surgical system. For example, a UID may be arranged to open/close the grasper (of the end effector 23) of the ultrasonic instrument, and/or may be arranged to adjust a spatial position (in space) of the grasper based on user input (e.g., the position of the UID).

Figure 3:
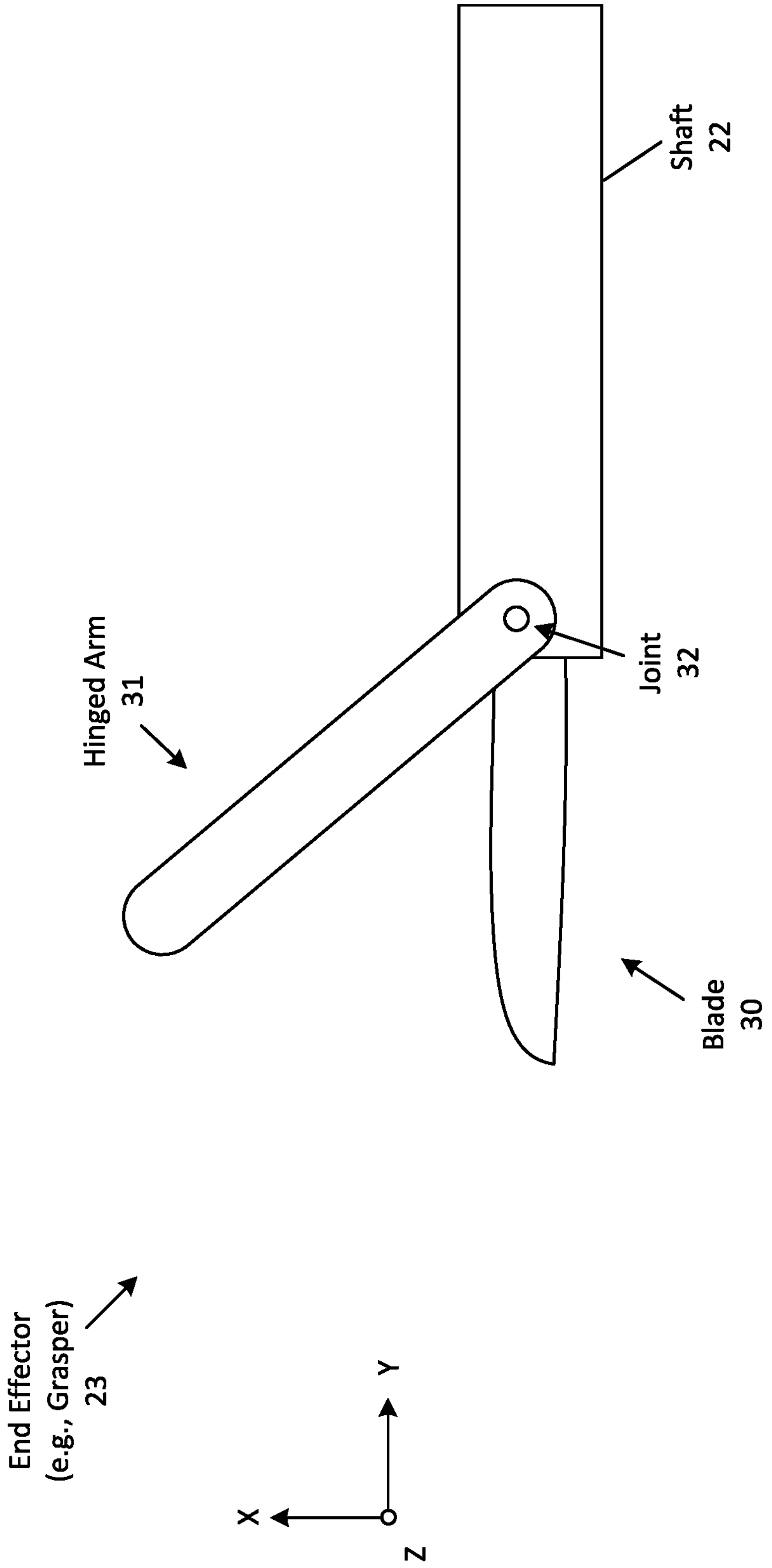
FIG. 3 shows an end effector of the ultrasonic instrument of FIG. 2.

Turning to FIG. 3, this figure shows the end effector 23 of the ultrasonic instrument of FIG. 2. Specifically, this figure shows that the end effector is a grasper (or grasping device) that includes a blade (or tip) 30 as one jaw and a hinged arm (or jaw) 31 that is rotatably coupled to a joint (or robotic wrist) 32, which is coupled to a distal end of the shaft. In another embodiment, the (e.g., joint 32 of the) end effector 23 may be a part of a portion (distal end) of the shaft 22. In another embodiment, the joint 32 may be a part of the blade 30. In one embodiment, the grasper (or a part of the grasper) is received through the shaft 22. For instance, the blade may be received (and extend) through the shaft and is arranged to couple to the tool drive (e.g., of the hand grip 21), at (or towards) a proximal end of the shaft.

The hinged arm 31 may be rotatably coupled (at the joint 32) to the shaft 22, and may be arranged to rotate about a rotational (Z-)axis (e.g., in the Z-direction). Specifically, the grasper may be arranged to open and close based on the rotational position of the hinged arm about the rotational axis of the joint with respect to the blade (and/or shaft). For example, the grasper is arranged to open (or is in an opened position) when the hinged arm is rotated away from the blade (e.g., by a threshold distance). While in this position, the end effector may be orientated whereby an object, such as tissue, may be disposed between the blade and the hinged arm (e.g., by moving the end effector about the object). The grasper may be closed (or in a closed position), when the hinged arm rotates towards the blade (e.g., within the threshold distance), whereby the grasper may grab the object between the blade and the hinged arm. As described herein, the hinged arm may be arranged to apply pressure against a grasped object (e.g., squeezing the object between the jaws) in order to grab and/or perform a dissection upon the object. In another embodiment, the hinged arm 31 may be rotatably coupled to (a portion of) the blade. In one embodiment, the blade 30 and the hinged arm may be received through the shaft such that the arm (and/or the blade) are coupled to another shaft that is passed through the shaft 22.

As described herein, the blade 30 may be a jaw of the grasper. In particular, the blade is a jaw that may not rotate (e.g., about the Z-axis) with respect to the end effector. The blade may be arranged to vibrate along a longitudinal (Y-)axis (in the Y-direction) of the blade to produce heat while the ultrasonic instrument is in a high-power (or heating) state (or mode). In particular, the blade may be driven (e.g., by the tool drive of the hand grip 21) to move back and forth (e.g., linearly) along the longitudinal axis of the end effector (and through the shaft, as described herein), so as to repeatedly displace the blade 30 at a (e.g., constant) frequency. Specifically, the blade may vibrate (e.g., reciprocate back and forth) over an excursion (or displacement) in which the blade moves a distance (e.g., forward or away from the end effector) from a starting position, and then moves the distance back. In one embodiment, the excursion may be a distance the blade moves from a starting position to an extended position. In another embodiment, the excursion may be the distance the blade moves forward and backward.

As described herein, the blade may produce frictional heat while vibrating against an object. Specifically, the blade may come into contact with tissue while the grasper is squeezing tissue between the two jaws 30 and 31, and may vibrate against the tissue. As the blade vibrates, the end effector may cut and/or cauterize the tissue, as described herein. In one embodiment, the blade may vibrate differently (e.g., over different excursions) based on a power state of (e.g., how much power is being provided to) the ultrasonic instrument. More about the vibrating blade and the power states of the ultrasonic instrument are described herein.

As described thus far, the end effector 23 may be a grasper. In another embodiment, the end effector may be any type of tool that may be designed to be manipulated by the (e.g., hand grip 21 of the) ultrasonic instrument. For example, the end effector may be an endoscope, a stapler, etc.

Turning back to FIG. 2, the generator 25 is configured to control and provide power to ultrasonic instrument to control (e.g., heat) the end effector 23 while the instrument is coupled to the generator and being used by an operator (e.g., during a laparoscopic surgery to manipulate tissue and/or perform one or more surgical tasks upon tissue, such as to cut and seal vessels and/or to cut, grasp, and dissect tissues). In particular, the generator may provide power to the ultrasonic instrument, such that the (e.g., ultrasonic instrument of the) surgical system 1 may operate in one of one or more power states (or cycles). For example, the generator may provide power to the instrument such that the ultrasonic instrument is in a "high-power" state (or "heating state") in which the instrument draws power (or current) from the generator (e.g., at a particular voltage) to cause the end effector 23 to produce heat. For example, the generator may provide (e.g., a first) current (or input current) to the (e.g., tool drive of the) hand grip of the ultrasonic instrument, which may use this current to drive the blade 30 to vibrate (or oscillate) over a (first) excursion (and at a particular frequency). Frictional heat may be produced by the end effector while the blade of the end effector is vibrating over this excursion up against an object, such as tissue, and may be used to cut and/or cauterize the object, as described herein.

In another embodiment, the ultrasonic instrument may be arranged to operate in a "low-power" state (or "cooling state") in which the ultrasonic instrument no longer draws the (sufficient or as much) power provided by the generator, while the instrument was in the high-power state, to heat the end effector. Specifically, while in this state, the generator may be configured to provide less power to the ultrasonic instrument than the power provided by the generator while instrument was in the high-power state, such that the end effector does not produce heat (e.g., when in contact with an object). In particular, the generator may provide less current (e.g., a second current) to the ultrasonic instrument than the (first) current provided by the generator while the instrument operates in the high-power state, and as a result, this does not cause the end effector to produce heat (or as much heat as when the ultrasonic instrument is in the high-power state). As a result, the ultrasonic instrument may begin to cool once it enters the low-power state from the high-power state. Ultimately, if kept in the low-power state, a temperature of the ultrasonic instrument may drop to (at least or below) a threshold temperature (e.g., room temperature). In one embodiment, the second current may be less than a predefined threshold current. In one embodiment, the blade may vibrate at a same frequency in the low-power state as in the high-power state. In another embodiment, the blade may vibrate the same within a tolerance frequency range.

As a result, of the lesser current provided to the instrument while in the low-power state, the blade of the end effector may be driven differently by the tool drive of the hand grip 21 than when the instrument is in the high-power state. In particular, the blade may vibrate over a different excursion than over which the blade vibrates while the instrument is in the high-power state. For instance, while in the high-power state, the blade may vibrate over the first (e.g., high) excursion, which may cause the blade to produce heat when pressed against an object, whereas, while in the low-power state, the blade may vibrate over a second (e.g., lower) excursion, which may be less than the first excursion (e.g., the blade being displaced less along the longitudinal Y-axis than in the first excursion). In some embodiments, the second excursion may be less than a minimum threshold (e.g., at which the blade would produce heat if the blade were to vibrate over the minimum threshold). In one embodiment, the end effector may not produce frictional heat, while vibrating over this lower excursion and while up against (in contact with) an object (e.g., while the grasper is squeezing the object), such as a blood vessel. In one embodiment, the resonance frequency is maintained within a tolerance range regardless of which power state the instrument is operating.

In one embodiment, the difference in vibration of the end effector may be based on the amount of power that is being drawn by the ultrasonic instrument while in the different states. For instance, the excursion at which the blade is displaced while it oscillates may be based on (e.g., proportional to) the power drawn by the instrument, whereby more power drawn by the instrument may cause the blade to vibrate over the high excursion. Conversely, while the ultrasonic instrument is in the low-power state the instrument may draw less power that causes the blade to vibrate less (than while the instrument is in the low-power state). As a result of oscillating over a lesser displacement, the blade may not produce frictional heat (e.g., while in contact with tissue). In another embodiment, the blade may produce some frictional heat while in the low-power state and in contact with an object, but may be less than the heat produced while the instrument is in the high-power state. In this case, this produced frictional heat may not be enough to cut and/or seal tissue. In some embodiments, as a result of operating in the low-power state, the end effector of the ultrasonic instrument may enter a cooling cycle, whereby the heat produced by the end effector while the instrument was in the high-power state dissipates (e.g., over a period of time). In another embodiment, the blade may not vibrate (e.g., the tool drive may not drive the blade) while in this low-power state.

In one embodiment, the system may enter (or operate in) at least one of the power states based on user input (e.g., received by the generator 25). In particular, the generator may provide power to the ultrasonic instrument based on receiving user input into one or more input devices (e.g., input into a foot petal, an UID that is controlled by an operator and communicatively coupled with the system 1, and/or input at the hand grip 21 of the ultrasonic instrument). The provided power based on the user input may put the ultrasonic instrument in the high-power state in which the ultrasonic instrument draws power from the generator to heat the (e.g., blade 30 of the) end effector 23. For example, when the generator receives (a first) user input (e.g., by the operator pulling on or pressing a trigger on the hand grip 21), the generator may provide current to the (e.g., tool drive of the) ultrasonic instrument, which uses the current to drive the end effector, as described herein. Thus, in the case where the trigger controls the hinged arm of the end effector, the generator is configured to provide the current when the hinged arm is moved (e.g., towards the blade 30 by at least a threshold distance). In another embodiment, the system may enter the low-power state based on another (e.g., second) user input (e.g., receiving input from a different input device coupled to the generator, such as a foot pedal).

In some embodiments, the ultrasonic instrument may be arranged to switch between the high-power state and the low-power state. As described herein, the instrument may operate in the high-power state while the generator is receiving user input (e.g., the user pulling on or pressing a trigger on the hand grip). The instrument may operate in the low-power state in response to the generator no longer receiving user input. For instance, the ultrasonic instrument may switch from the high-power state into the low-power state in response to the user releasing the trigger on the hand grip, the generator may transition between the two states). In one embodiment, the instrument may operate in the low-power state while the operator is not actively using the instrument to perform ultrasonic instrument operations, as described herein. Specifically, the system may enter the low-power state, while user input is not received into one or more input devices that are used by the operator to enter the high-power state. Once, however, the operator wishes to actively use the ultrasonic instrument, the ultrasonic instrument may switch back into the high-power state (e.g., in response to user input). In another embodiment, the instrument may operate in the low-power state in response to receiving user input (e.g., the user pressing a button on a UID). In another embodiment, the instrument may operate in this state for a period of time. As described herein, the surgical system is configured to determine a temperature of the end effector while in the low-power state (e.g., after switching from the high-power state) in order to notify an operator of the temperature, which may be high due to the instrumenting having operated in the high-power state. Once the end effector cools to a particular temperature (e.g., equal to or less than a predefined temperature), the generator may deactivate the instrument by ceasing to provide the lower current, since at this temperature the end effector may not cause thermal injuries if it were to come into contact with tissue.

In one embodiment, the generator may provide different levels of current to heat up the blade, which may be based on user input. For instance, the generator may receive a first user input (e.g., from one petal coupled to the generator) and, in response, provide the ultrasonic instrument with a maximum (allowable) amount of current. The ultrasonic instrument may then drive the end effector over a maximum (e.g., predefined) excursion, which may result in the end effector producing heat at a (first) high temperature. When the generator receives a second user input (e.g., from another petal coupled to the generator), however, the generator may provide a lesser amount of current to the ultrasonic instrument. As a result, the ultrasonic instrument may draw less power to cause the end effector to vibrate over a (second) lower excursion, which may be lower than the first excursion over which the blade vibrates in response to the first user input. This lower excursion, however, may cause the end effector to heat at a lower temperature than the first temperature of the end effector when the ultrasonic instrument draws more current (in response to the generator receiving the first user input). By heating the end effector to different temperatures, different types of tissues may be cut and/or cauterized. For example, fattier tissues may require the end effector to be hotter (having the first temperature), whereas thinner (and less fatty) tissues may require less heat (having the second temperature), in order to cut and/or cauterize the tissues. In another embodiment, the generator may be configured to provide one current while in the high-power state (e.g., to drive the end effector over the first high excursion).

As described herein, the ultrasonic instrument may be activated (e.g., operate in the high-power state) based on whether the end effector is in a closed position so as to grasp an object (e.g., a piece of tissue). For example, the ultrasonic instrument may be (e.g., user) activated, such that the ultrasonic instrument may operate in the high-power state so as to draw enough current to cause the end effector to produce heat. In particular, the generator may activate the ultrasonic instrument upon receiving user input to close the end effector (e.g., to cause the hinged arm 31 to move within a distance of the blade 30). Once user input is received to move the hinged arm, the generator may be configured to provide (e.g., enough) power to activate the instrument, as described herein. In some embodiments, the generator may activate the instrument based upon a determination that the hinged arm and/or the blade are in contact with an object. For instance, the ultrasonic instrument may include one or more sensors (e.g., force/pressure sensors), that detect a presence of an object and/or detect that an object is in contact with both arms. In particular, upon determining that the grasper is squeezing an object (based on a detected pressure from the sensor being above a threshold), the generator may enter the high-power state. Upon making this determination, the generator may provide the first current to oscillate the blade in order to cause the blade to produce heat. Once the pressure reading drops below the threshold (meaning that the object has been released by the grasper), the generator may switch to the low-power state.

In one embodiment, the (e.g., generator of the) surgical system may be configured to determine one or more characteristics of the (end effector of the) ultrasonic instrument, while the instrument is in one or more power states. For example, the generator may be configured to keep track (or monitor) characteristics, such as an input voltage, an input current, a resonance state, a resonance frequency, and/or a (e.g., mechanical) impedance of the (e.g., end effector of the) ultrasonic instrument. In one embodiment, the "resonance frequency" may be the frequency at which an object, such as (e.g., a portion of the end effector) of the ultrasonic instrument, (e.g., naturally) vibrates. In this case, the resonance frequency may be the frequency at which the end effector vibrates while end effector is in a heating state and/or a cooling state. In some embodiments, the resonance frequency of the end effector may change based on the temperature of the (e.g., blade 30 of the) end effector. More about the resonance frequency is described herein. In one embodiment, the generator may be configured to monitor at least some of these characteristics of the instrument, while the instrument operates in the high-power states. In addition, the system may be configured to determine (at least some of) these characteristics while the instrument is in the low-power state (cooling cycle or cooling period) due to the instrument drawing at least some power. For example, the generator may determine the resonance frequency and the impedance of the (e.g., blade 30 of the) end effector, while in the low-power state. More about determining these characteristics is described herein.

In one embodiment, the surgical system may include additional components. For example, the system may include a cable that connects the generator to the ultrasonic instrument (e.g., the ultrasonic transducer, which is configured to convert an electric current drive signal to mechanical vibrations). In one embodiment, the ultrasonic transducer may be connected to a waveguide, which is connected to the blade 30 of the end effector 23.

Also shown, the generator 25 also includes a display 24, which is arranged to display information regarding the operation of the ultrasonic instrument. For instance, the display may present temperature information, which state the ultrasonic instrument is currently in, and one or more of the characteristics described herein.

Figure 4:
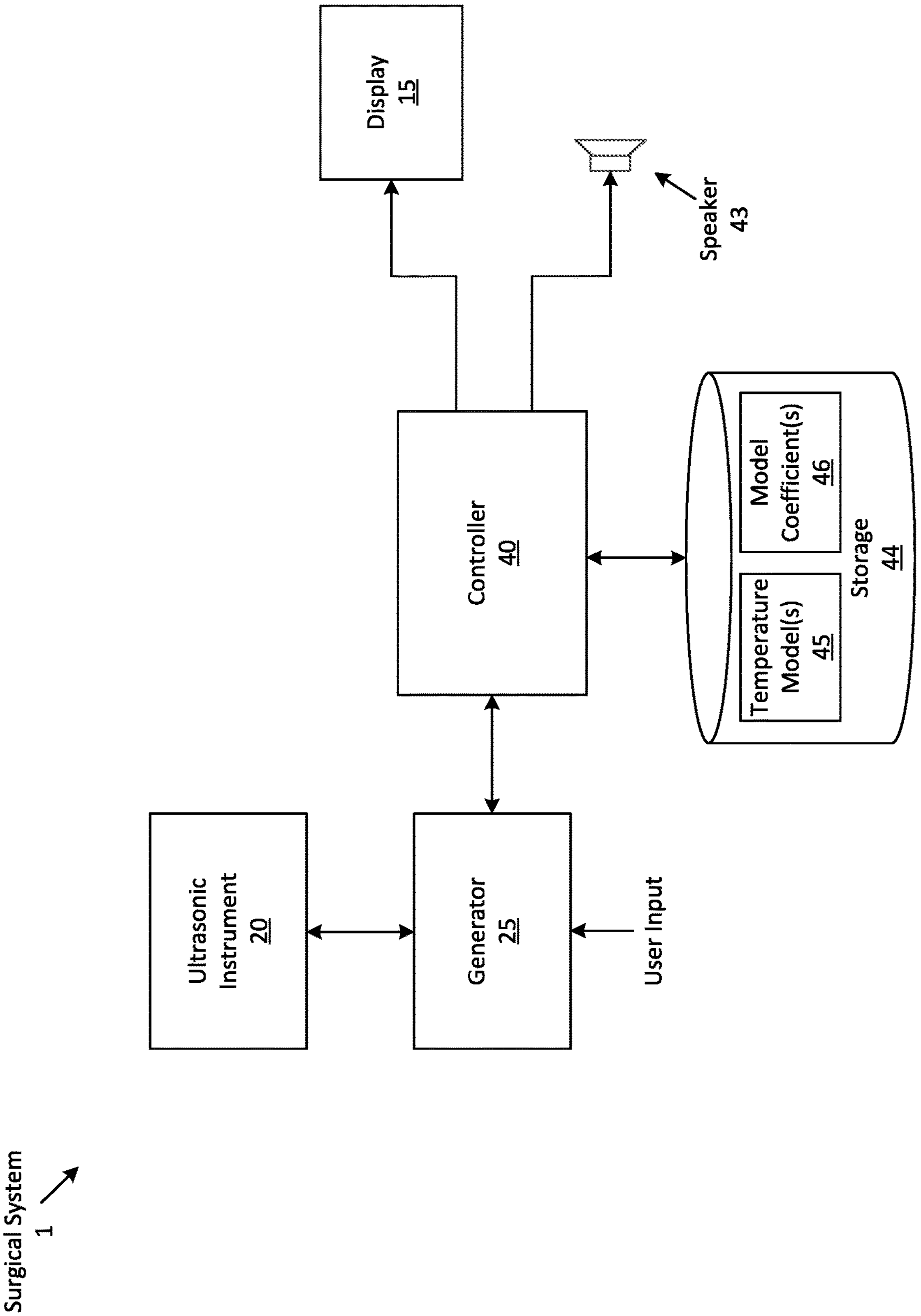
FIG. 4 is a block diagram of the surgical system according to one embodiment.

FIG. 4 is a block diagram of the surgical system 1 according to one embodiment. The system includes the ultrasonic instrument 20, the generator 25, a controller 40, storage (memory) 44, the display 15, and a speaker 43 (that may be a stand-alone speaker or a part of an electronic device of the system, such as the user console 2). In one embodiment, the system may include more or less elements, such as having more than one display, and/or not having the speaker. Although the elements are illustrated as being separate, at least some may be a part of (or integrated) with one another. For example, the storage 44 may be a part of (e.g., as internal memory of) the controller 40. As another example, the controller 40 may be a part of the generator 25, or may be a part of a separate electronic device, which may be communicatively coupled with the generator 25.

Examples of the storage 44 (e.g., non-transitory machine-readable storage medium) may include read-only memory, random-access memory, CD-ROMS, DVDs, magnetic tape, optical data storage devices, flash memory devices, and phase change memory. The storage 44 includes one or more temperature models 45, which may be used by the (e.g., controller 40 of the) surgical system 1 to determine (estimate) one or more temperatures of (at least a portion of) the ultrasonic instrument 20. In particular, the temperature models may be configured to output a temperature value (e.g., in Celsius) in response to input of one or more parameters, by the controller. In one embodiment, at least some of the models 45 may represent temperature estimates with respect to resonance frequency. In some embodiments, one or more of the models 45 may output a temperature responsive to one or more characteristics of the ultrasonic instrument, such as resonance frequency, as input. More about the use of the temperature models is described herein.

In one embodiment, one or more temperature models 45 may be predefined models, such as being determined (or created) in a controlled setting (e.g., in a laboratory), and provided to the surgical system, such as being downloaded from a remote server over a network (e.g., the Internet). In one embodiment, the temperature models may be machine learning (ML) models that may be (e.g., continuously) trained to estimate temperature based on one or more sets of training data. In one embodiment, the ML models may be any type of ML model, such as a deep neural network (DNN), a convolution neural network (CNN), etc. As described herein, at least some of the temperature models may be used by the controller 40 to estimate the temperature of the end effector of the ultrasonic instrument 20.

In another embodiment, the models may include different types of models based on a (current) state of the ultrasonic instrument, which may be used by the surgical system to estimate the temperature of the end effector 23. For example, the models 45 may include one or more cooling temperature models that may be used by the system to estimate the temperature of the end effector while the instrument is in a cooling state, and/or may include one or more heating temperature models that may be used by the system to estimate the temperature of the end effector while the instrument is in a heating state. In another embodiment, the models 45 may include models based on the state of the end effector of the ultrasonic instrument. For example, the models 45 may include one or more models that may be used by the system to estimate the temperature of the end effector while the end effector is "in air" (e.g., not touching an object). In particular, the end effector may be in-air while an operator is holding the (e.g., hand grip 21 of the) ultrasonic instrument 20 such that open space entirely surrounds (e.g., the blade 30 of) the end effector. In one embodiment, the end effector may be in contact with one or more objects while in-air. For example, an object may be (inadvertently) attached to a portion of the blade, which may be based on the temperature of the blade. In another embodiment, the models 45 may include one or more models that may be used by the system to estimate the temperature while the end effector is in contact with an object. In this case, the end effector may be considered in contact with an object when an operator manipulates the hand grip such that at least a portion of the end effector is pushed up against the object by the operator. More about the different models is described herein.

The storage 44 also includes one or more model coefficients 46, which may be terms, values, and/or functions that may be used by one or more of the temperature models 45 to compute an estimated temperature. In one embodiment, the model coefficients may be based on characteristics of the ultrasonic instrument. For example, the coefficients may include functions with respect to characteristics (e.g., resonance frequency), such that one or more coefficients may be estimated as output of a function responsive to one or more characteristics as input. In some embodiments, the model coefficients may be numerical values. In another embodiment, the model coefficients 46 may be stored in a lookup table that associates model coefficients with one or more characteristics. In which case, the controller may be configured to estimate model coefficients by performing a table lookup into the data structure using one or more determined characteristics of the ultrasonic instrument. More about determining coefficients is described herein.

In one embodiment, the storage may include one or more models and/or one or model coefficients that are associated with a particular device (e.g., being device specific). For example, different ultrasonic instruments may have different physical characteristics, which may affect rate at which temperature may increase or decrease. As a result, the storage may include one or more models and/or model coefficients for different ultrasonic instruments. For instance, the storage may include a first heating model for a first instrument, and include a second heating model for a second instrument.

In some embodiments, controller 40 may be a special-purpose processor such as an application-specific integrated circuit (ASIC), a general purpose microprocessor, a field-programmable gate array (FPGA), a digital signal controller, or a set of hardware logic structures (e.g., filters, arithmetic logic units, and dedicated state machines). In one embodiment, the controller may be a part an electronic device, such as the console computer system 16, the control tower 3, and/or the user console 2. Although illustrated as being a single component, in another embodiment, the controller may comprise one or more electronic components (e.g., processors, memory, etc.) that are communicatively coupled on a single electronic device (such as the console computer system 16), or across multiple devices (e.g., communicating over a wireless computer network). In some embodiments, the controller may be a part of a separate device, such as a part of a remote server that is in communication with one or more electronic devices. In another embodiment, the controller may be a part (e.g., at least partially integrated within) the generator 25, as described herein. In which case, at least some of the other elements (e.g., the speaker and display) may also be a part of (integrated within) the generator. As a result, at least some of the operations performed by the controller described herein may be performed by the generator 25.

In one embodiment, the controller may be configured to perform temperature estimation operations for the surgical system 1 to determine a (e.g., real-time) temperature (or a change in temperature) of the (e.g., end effector of the) ultrasonic instrument, while the instrument is in one or more states, such as a cooling state (e.g., which may be a low-power state, where the blade of the end effector is not being actively heated in order to cut and/or seal tissue). Specifically, the controller may determine the temperature based on one or more characteristics of the ultrasonic instrument that are determined while the instrument is in the cooling state, such as a resonance frequency of the (e.g., blade of the) end effector. The controller may determine the temperature using one or more temperature models 45, whereby a temperature model may output an estimated temperature of the blade based on (in response to) the resonance frequency, as an input. For example, the controller may determine whether the end effector of the ultrasonic instrument is in a heating state or a cooling state, which may be based on estimated characteristics (e.g., voltage, current, etc.) of the instrument. Responsive to determining that the system is in a heating state, the controller may estimate the temperature of the end effector based on output of a first temperature model (e.g., a heating model) based on one or more characteristics, such as the resonance frequency of the instrument, and responsive to determining that the system is in a cooling state, the controller may estimate the temperature of the end effector based on output of a second temperature model (e.g., cooling model) based on the one or more characteristics. The controller may be configured to present (e.g., display) a notification based on the estimate temperature. As a result, the system may estimate the temperature of the end effector regardless of what state the instrument is operating, and may display the estimated temperature to the operator (e.g., in real-time). More about the operations performed by the controller are described herein.

In one embodiment, (at least some) of the temperature estimation operations may be performed by the controller while the end effector is in the heating state and/or in the cooling state. As described herein, the temperature estimation operations may be performed during the cooling state, and while the end effector is "in air", meaning that the blade is not in contact with an object (e.g., based on operator manipulation), such as tissue (and/or is not at least partially submerged in liquid). In particular, as described herein, during a laparoscopic surgery a cavity may be created within a patient's abdomen using one or more gases. In which case, the temperature estimation operations may be performed while the (blade of the) end effector is within the cavity, but while (e.g., the operator holds the ultrasonic instrument such that) the end effector is suspended within the one or more gases inside the cavity, or outside the cavity.

In another embodiment, the temperature estimation operations may be performed while the end effector of the ultrasonic instrument is in contact with an object. In one embodiment, one or more characteristics of the ultrasonic instrument may change based on whether the (e.g., blade of the) end effector is in-air or is touching an object. For example, when the blade is touching an object, its resonance frequency (or damped natural frequency, $\omega_d$) may increases, due to an increase in the blade's stiffness, k, as opposed to when the blade is in the air. In particular, damped natural frequency may be seen as $$\omega_d = \omega_n\sqrt{1-\gamma^2}$$

where $\gamma$ is a damping ratio and $\omega_n$ is the blade's undamped natural frequency, which may be written as dependent on the stiffness of the blade as $$\omega_n^2 = \frac{k}{m}$$

where m is the mass of the blade. In one embodiment, m may include the mass of the blade and any objects (e.g., residual tissue) that is attached to the blade. The damping ratio may be written as $$\gamma = \frac{\left(\frac{b}{m}\right)}{2\omega_n}$$

in which b is the damping on the blade. Thus, as k increases (e.g., due to the blade touching an object), $\omega_n$ increases, and therefore $\gamma$ decreases, which both lead to an increase in $\omega_d$.

In one embodiment, at least some of the operations performed by the controller may be implemented in software (e.g., as instructions) stored in memory of the surgical system (e.g., the storage and/or (internal) memory of the controller) and executed by the controller and/or may be implemented by hardware logic structures. In one embodiment, at least some of the operations performed by the controller may be performed each time the instrument enters a state (or switches between states, such as switching between the cooling state to the heating state). In another embodiment, the controller may periodically perform (e.g., every second) one or more operations described herein while the surgical system is in a particular state, such that the estimated temperature may be presented to the operator during a surgical procedure in which the ultrasonic instrument is being used.

As shown, the generator may receive user input (e.g., via one or more electronic devices coupled to the generator) for causing the generator to perform one or more operations. For instance, the user input may be received via the ultrasonic instrument (e.g., when the user pulls on a trigger of the hand grip) in order to cause the generator to provide current that causes the ultrasonic instrument to switch from the low-power state to the high-power state, as described herein.

FIGS. 5-8 and 10 are flowcharts of processes 50-80 and 100, respectively, that each include one or more operations that may be performed by the (e.g., controller 40 and/or generator 25 of the) surgical system 1 to perform temperature estimation operations, as described herein. Specifically, the operations described herein may be performed while the ultrasonic instrument is in use by an operator during a surgical procedure. For example, at least some operations may be performed while the instrument is being used to perform a surgical task and/or may be performed before (and/or after) a task has been performed. In another embodiment, at least some of the operations may be performed by (e.g., one or more processors of) the generator 25. Thus, these figures will be described with reference to FIGS. 1-4. In one embodiment, at least some of these operations may be performed while the ultrasonic instrument is in one of one or more states described herein. For instance, the operations described in process 60 of FIG. 6 may be performed while the ultrasonic instrument is in a heating state. As another example, at least some operations of processes 70 and 80 of FIGS. 7 and 8, respectively, may be performed while the ultrasonic instrument is in a cooling state.

Figure 5:
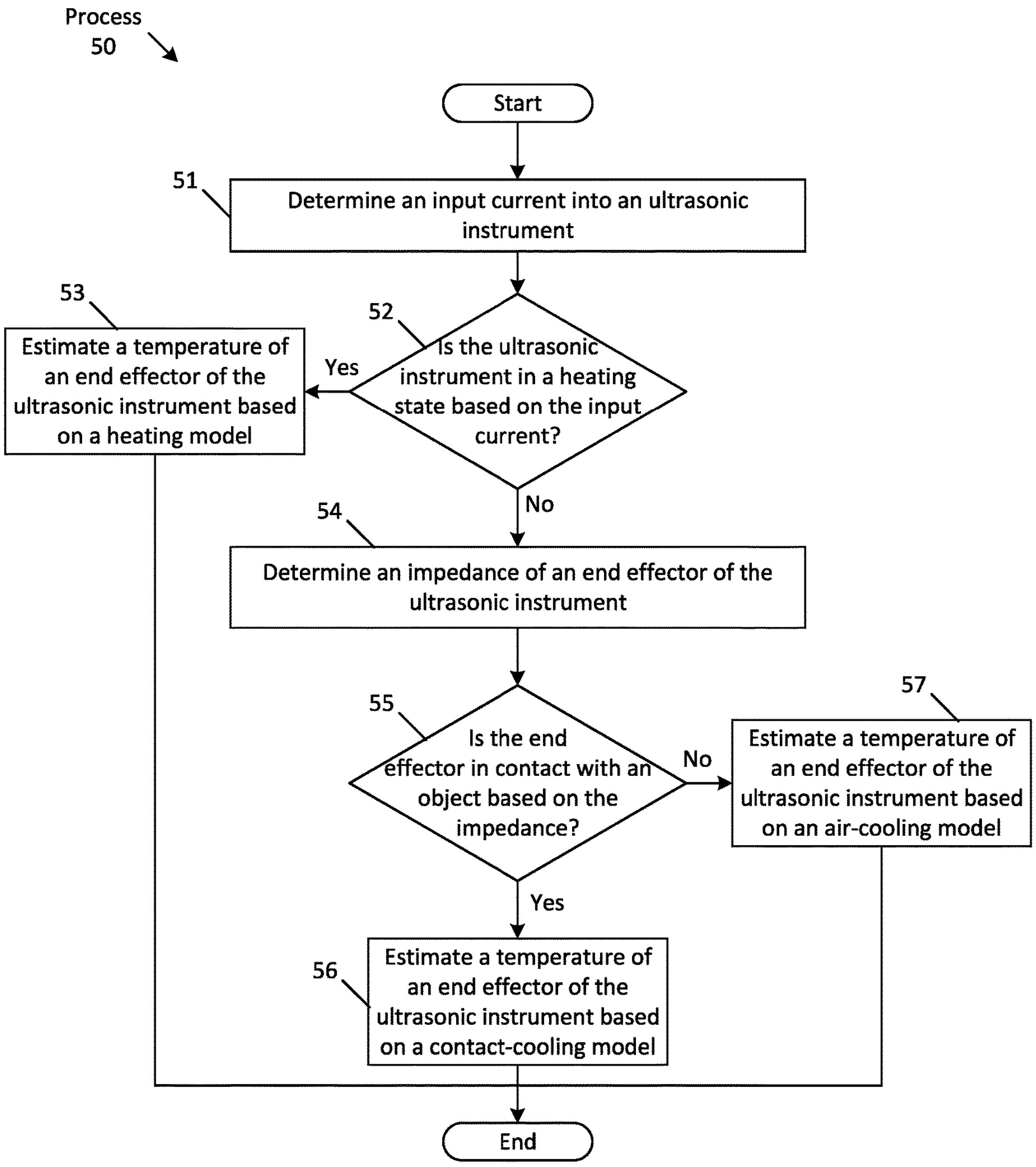
FIG. 5 is a flowchart of one embodiment of a process for estimating a temperature of an end effector of an ultrasonic instrument.

Turning FIG. 5, this illustrates a flowchart of one embodiment of the process 50 for estimating a temperature of an end effector of an ultrasonic instrument. Specifically, this process may (at least partially) be performed by the controller 40 to determine which configuration (or state) the end effector of the ultrasonic instrument is operating in order to estimate the temperature of the end effector, and to estimate the temperature based on the determined configuration.

The process 50 begins by the controller 40 determining an input current into the ultrasonic instrument 20 (at block 51). For example, the controller 40 may receive the input current from one or more sensors (e.g., a current sensor) of the (e.g., instrument 20 of the) surgical system 1 that may be monitoring current that is being drawn by the ultrasonic instrument. In another embodiment, the controller 40 may receive sensor data (e.g., characteristics), which may include the input current, from the generator 25 that may be configured to monitor the data.

The controller 40 determines whether the ultrasonic instrument is in a heating state based on the input current (at decision block 52). In particular, the controller is determining whether the end effector of the ultrasonic instrument is in a heating state (e.g., being used to cut tissue) or in a cooling state (e.g., being held in-air by the operator in order to allow the instrument to cool after being used to perform a surgical task). The controller 40 may determine which state the instrument is in based on the current that is being drawn by the instrument. For example, as the ultrasonic instrument is in a heating cycle, the instrument may draw a significant amount of current. In particular, the instrument may draw more current as heat is produced by the end effector, than an amount of current drawn by the instrument while in a cooling cycle, as described herein. In which case, the controller may be configured to determine whether the instrument is in the heating state based on whether the input current is greater than a current threshold. In one embodiment, the current threshold may be between 0.1 mA-4 mA. If it is determined that the instrument is in the heating state (e.g., based on the input current being greater than the current threshold), the controller 40 estimates a temperature of the end effector of the ultrasonic instrument based on a heating model (at block 53). For example, the controller may use a heating model from models 45 stored within storage 44 to predict a temperature of the end effector. More about estimating the temperature while the instrument is in a heating state is described in herein.

If, however, the ultrasonic instrument is not in the heating state (e.g., based on the input current being less than the current threshold), the controller may determine that the instrument is in a cooling state. The controller 40 may be configured to determine an impedance of the end effector of the ultrasonic instrument (at block 54). In particular, the impedance may be determined while the instrument is in the cooling state. As described herein, the impedance may be a mechanical impedance which may be determined by the controller 40 using one or more of the (monitored) characteristics of the ultrasonic instrument, such as the input current and/or input voltage of the end effector. For example, the controller may use the input current of the ultrasonic instrument (e.g., used to drive a blade of the end effector) and the input current, and determine the mechanical impedance based on these characteristics (e.g., based on Ohm's law). In one embodiment, the input voltage may change to maintain the current that may be set to compensate for changes in the impedance. In another embodiment, the controller may determine the impedance by applying one or more of the characteristics into a (e.g., predefined) impedance model (e.g., an electro-mechanical model of the impedance of at least a portion of the end effector), which outputs the mechanical impedance. In another embodiment, the controller may use any known method to determine the impedance of the blade. In one embodiment, the controller may receive the impedance from the generator 25.

The controller 40 determines whether the end effector is in contact with an object based on the impedance (at decision block 55). Specifically, the controller 40 is determining whether the end effector is being air-cooled or is being contact-cooled. In particular, the controller is determining whether the end effector is in contact with an object (e.g., by an operator manipulating the ultrasonic instrument such that the end effector is touching an object), such as tissue, or is in the air (e.g., where the ultrasonic instrument is manipulated by the operator to be suspended in air and not being manipulated by the operator to come into contact with an object). In one embodiment, to determine whether the end effector is in contact with an object, the controller may determine whether the impedance is greater than an impedance threshold. Responsive to determining that the impedance is greater than the threshold, the controller may determine that the end effector is in a cooling state while in contact with an object, the controller may be configured to estimate a temperature of the end effector of the ultrasonic instrument based on a contact-cooling model (at block 56). For example, upon determining that the end effector is in contact with an object, the controller may be configured to determine a cooling model (e.g., from models 45) that accounts for the end effector being in contact with an object, and may be configured to determine the temperature of the end effector using the model. More about estimating a temperature of the end effector while the ultrasonic instrument is in the cooling state and in contact with an object is described herein.

If, however, the impedance is less than the impedance threshold, the controller determines that the end effector is in the cooling state while in-air. The controller estimates a temperature of the end effector of the ultrasonic instrument based on an air-cooling model (at block 57). In one embodiment, the air-cooling model (which may be retrieved from models 45 in storage 44) used by the controller may be different than the contact-cooling model, described herein. For example, the air-cooling model may be a polynomial model, whereas the contact-cooling model may be an exponential model. More about estimating the temperature of the end effector while the ultrasonic instrument is in the cooling state and in-air is describe herein.

As a result, the controller 40 may be configured to determine which state the ultrasonic instrument is in, such as whether the instrument is in the heating state, the cooling state while the end effector is in contact with an object, or the cooling state while the end effector is in-air, and may be configured to estimate the temperature based on the state of the instrument. In one embodiment, the controller may periodically and/or continuously perform at least some of these operations while the instrument is in use, such that the controller may estimate the temperature of the end effector while the instrument switches between the states in order to provide an operator with a real-time estimate of the temperature. Thus, the surgical system may effectively, efficiently, and seamlessly provide the temperature estimate to an operator as the instrument switches between states.

Figure 6:
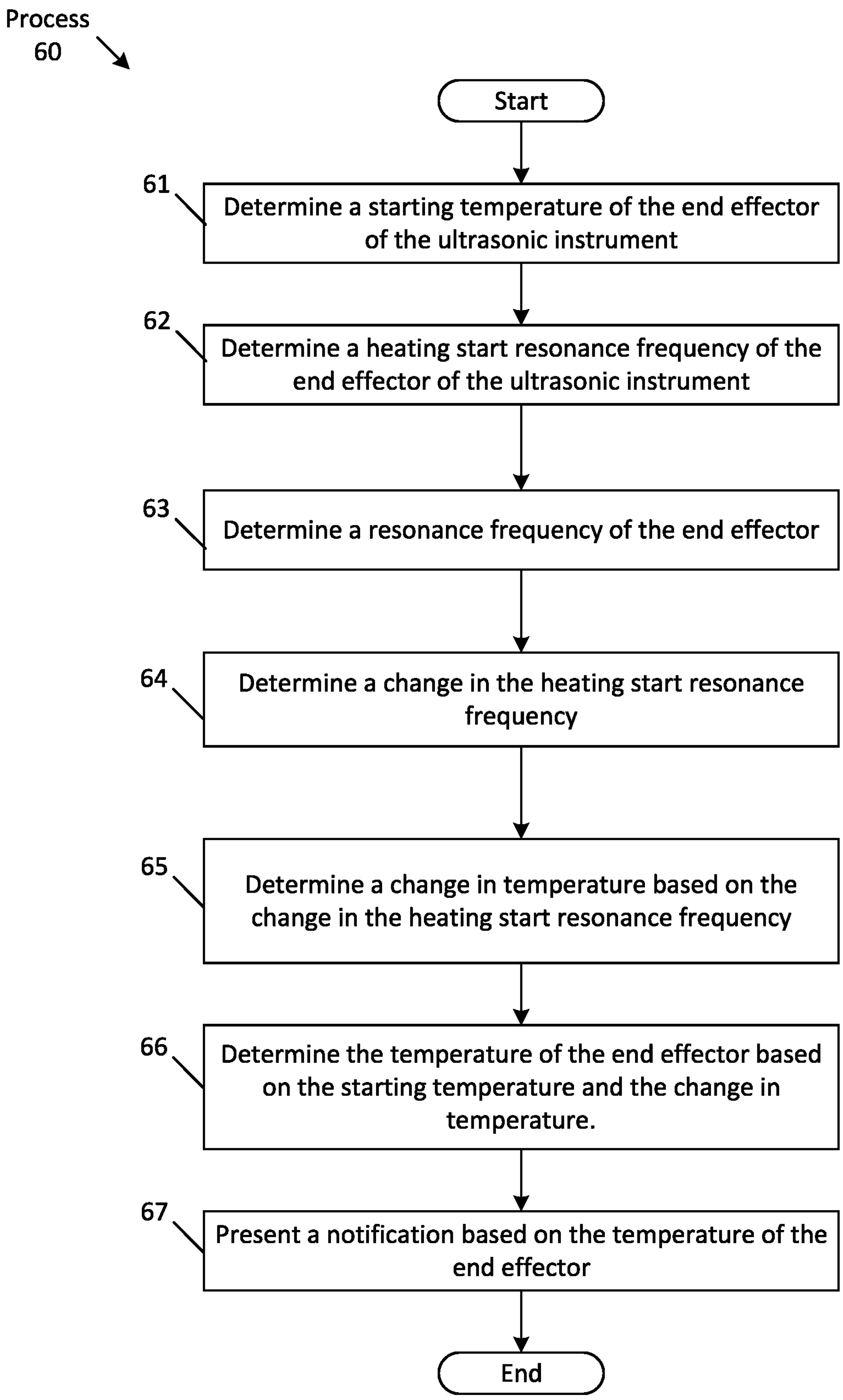
FIG. 6 is a flowchart of one embodiment of a process for estimating a temperature of an end effector of an ultrasonic instrument while the end effector is in a heating state.

FIG. 6 is a flowchart of one embodiment of a process for estimating a temperature of an end effector of an ultrasonic instrument while the end effector is in a heating state. In particular, at least some of the operations described in process 60 may be performed upon the controller 40 determining that the ultrasonic instrument 20 is in the heating state (e.g., at blocks 52 and 53 of process 50 in FIG. 5).

The process 60 begins by the controller 40 determining a starting temperature, $T_{Start}$, of the end effector of the ultrasonic instrument (at block 61). In particular, the controller may determine $T_{Start}$ at a (starting) time, which may be a time at which the end effector has (or is determined by the controller to have) entered the heating state. For instance, the controller may determine $T_{Start}$ upon the controller determining (or once the controller determines) that the ultrasonic instrument is in the heating state at decision block 52 in process 50 of FIG. 5 (e.g., once the input current of the ultrasonic instrument has exceeded a current threshold). In one embodiment, the controller may determine $T_{Start}$ at a time at which an input current of the ultrasonic instrument is monitored for determining that the instrument is in the heating state, as described in process 50 of FIG. 5.

In one embodiment, $T_{Start}$ may be determined by the controller 40 based on the environment in which the instrument is located. In particular, $T_{Start}$ may be determined to be (approximately or equal to) an ambient temperature of the environment. For example, $T_{Start}$ may be determined based on temperature data received from a (e.g., ambient) temperature sensor of the surgical system. In another embodiment, $T_{Start}$ may be based on a surgical site in which the end effector is located. For example, as described herein, these operations may be performed while the ultrasonic instrument is being used to perform a surgical task at a surgical site (e.g., within an abdomen of a patient) during a surgical procedure. In which case, the surgical system may determine $T_{Start}$ as a (e.g., measured or estimated) body temperature of the patient. In one embodiment, the controller may determine the environment in which the end effector is located based on sensor data captured by one or more sensors of the surgical system. For instance, the controller may be configured to perform an object recognition algorithm upon video data captured by one or more cameras of the system, and upon identifying the environment of the end effector (based on the object recognition algorithm), the controller may determine the temperature of the environment. As an example, the controller may perform a table lookup into a data structure that associates (e.g., ambient) temperatures with environments using the identified environment.

In another embodiment, $T_{Start}$ may be based on a temperature of the end effector that was previously estimated by the controller 40. As described herein, the surgical system may perform the operations described herein to estimate the temperature of the end effector as the system switches between states, such as switching between an air-cooling state and the heating state. In which case, the controller may estimate $T_{Start}$ as a temperature (e.g., a last temperature) estimated by the controller while the system was in a previous (e.g., the air-cooling) state before entering the current heating state. More about estimating the temperature while in a cooling state is described herein.

Returning to FIG. 6, the controller 40 determines a heating start (first) resonance frequency, $RF_{HS}$, of the end effector of the ultrasonic instrument (at block 62). In one embodiment, $RF_{HS}$ is the resonance frequency determined at the start time associated with $T_{Start}$. For example, $RF_{HS}$ may be a resonance frequency that is at a starting time at which the end effector enters (or transitions into) another state (e.g., such as the time at which the end effector enters the heating state. In one embodiment, $RF_{HS}$ may be determined (at least partially) contemporaneously as (or simultaneously as) $T_{Start}$ is determined (e.g., with respect to a clock of the surgical system).

In some embodiments, the controller (and/or generator) may determine the resonance frequency electronically. For example, the generator may sense voltage and current waveforms (and the difference in phase angle between the two waveforms) that are used to drive (e.g., the blade of) the end effector. Specifically, the ultrasonic instrument 20 (e.g., the tool drive) may include an ultrasonic transducer that is configured to vibrate the blade according to the input voltage and current waveforms. The frequency that produces a difference in phase angle of a threshold (e.g., zero) is the resonance frequency. In which case, the surgical system may be configured to determine $RF_{HS}$ using one or more characteristics, such as voltage and current that are sensed (or measured) at a time at which $T_{Start}$ is determined (or at the time at which characteristics are sensed that are used to determine $T_{Start}$). In another embodiment, other known methods may be used to determine the resonance frequency.

The controller 40 determines a (second) resonance frequency, RF, of the end effector (at block 63). In one embodiment, RF may be a subsequent resonance frequency determined by the controller after $RF_{HS}$ is determined (e.g., with respect to a clock of the surgical system). For instance, the controller may determine RF at a time that is subsequent to the starting time at which $RF_{HS}$ is determined. As an example, $RF_{HS}$ may be determined at a starting time (e.g., T=0 s), which may be a time at which the system enters the heating state, and may determine RF at a later time (e.g., T=1 s). The controller 40 determines a change in the heating start resonance frequency, $\Delta RF_{HS}$ (at block 64). In particular, the controller may determine $\Delta RF_{HS}$ based on a difference between $RF_{HS}$ (a first resonance frequency) and RF (a second resonance frequency), such as $\Delta RF_{HS}=RF_{HS}-RF$.

The controller 40 determines (estimates) a change in temperature, $\Delta T$, based on $\Delta RF_{HS}$ (at block 65). Specifically, the controller may use a heating model to determine $\Delta T$. For instance, the change in temperature may be output of a heating model based on $\Delta RF_{HS}$ as input into the model. In one embodiment, the controller may retrieve the heating model from the temperature models 45 stored in storage 44. For example, the controller may perform a table lookup into a data structure that includes the temperature models 45 based on one or more parameters. In particular, the controller may select a heating model from the temperature models 45 that is associated with the ultrasonic instrument 20. As described herein, the storage may include models that are device-specific. In which case, the controller may determine an identifier associated with the ultrasonic instrument and select the temperature model that is associated with the identifier. In one embodiment, the selected model may be a polynomial model, such as a third-order polynomial. In another embodiment, the heating model may be a second-order polynomial. In some embodiments, the heating model may be any type of model, such as an exponential model.

The controller determines the temperature, $T_H$, of the end effector based on $T_{Start}$ and $\Delta T$ (at block 66). In particular, the controller 40 may add (combine) the temperatures to determine the temperature of the end effector, such that $T_H=T_{Start}+\Delta T$. Thus, the controller estimates the temperature of the end effector based on the starting temperature of the end effector, the starting resonance frequency, and a subsequent resonance frequency. The controller 40 presents a notification based on the temperature of the end effector (at block 67). For example, the system 1 may display a pop-up notification on display 15 indicating the estimated temperature. As another example, the controller 40 may output an audible notification through the one or more speakers (e.g., speaker 43). For instance, the audible notification may be one or more sounds (e.g., a beep), which indicates the temperature of the end effector, such as a series of sounds that may indicate that the temperature is greater than a temperature threshold. In another embodiment, the notification may be a spoken word (e.g., "The instrument is at 300°!"). In another embodiment, any type of notification may be presented.

As shown, FIGS. 7 and 8 include several operational blocks that are included in (and described with respect to) FIG. 6, such as blocks 61, 63, and 67. For the sake of brevity, at least some of these operational blocks that were described with respect to FIG. 6 will not be described again with respect to FIGS. 7 and 8.

Turning to FIG. 7, this figure shows a flowchart of one embodiment of the process 70 for estimating a temperature of an end effector of an ultrasonic instrument while the end effector is in a cooling state. In one embodiment, the controller 40 may perform at least some of the operations of process 70 upon determining that the ultrasonic instrument is in a cooling state, as described in process 50 of FIG. 5. In another embodiment, the operations may be performed upon the controller 40 determining that the ultrasonic instrument transitions from a heating cycle to a (current) cooling cycle (e.g., when the user input is no longer received through the generator 25 to activate the end effector of the ultrasonic instrument to perform a surgical task, such as cutting and cauterizing tissue).

The process 70 begins by the controller 40 determining a starting temperature, $T_{Start}$, of the end effector of the ultrasonic instrument (at block 61). For example, the controller may define $T_{Start}$ as a temperature that was (e.g., last) estimated while the ultrasonic instrument was in a heating cycle, before entering the current cooling cycle. The controller 40 determines a cooling start resonance frequency, $RF_{CS}$, of the end effector of the ultrasonic instrument (at block 71). For instance, $RF_{CS}$ may be determined at a same starting time as $T_{Start}$ is determined. In another embodiment, $RF_{CS}$ may be determined upon the controller 40 determining that the ultrasonic instrument is in a cooling cycle (e.g., based on the input current of the ultrasonic instrument being less than or equal to a current threshold).

The controller 40 determines a (e.g., subsequent or second) resonance frequency, RF, of the end effector (at block 63). The controller determines an impedance, I, of the end effector (at block 72). For example, the impedance may be a mechanical impedance which may be determined by the controller 40 using one or more of the (monitored) characteristics of the ultrasonic instrument, such as an input current, as described herein. The controller 40 determines a corrected resonance frequency, $RF_{Corrected}$, based on the impedance, I, and the resonance frequency, RF (at block 73). In particular, $RF_{Corrected}$ may compensate for changes to one or more physical characteristics of the ultrasonic instrument, which may have occurred while the ultrasonic instrument was in a previous heating cycle. For instance, as described herein, the resonance frequency of the ultrasonic instrument may be proportional to the mass, m, of the instruments end effector (e.g., blade). During use of the end effector in a heating cycle, a portion of an object, such as tissue, may inadvertently attach to a portion of the blade. As a result, m may increase due to objects that have attached to the blade. Thus, the mass of the blade may increase while the end effector is in-air due to one or more portions of objects attaching to the blade. As a result, a measured resonance frequency may be inaccurate. Therefore, to account for changes to physical characteristics of the end effector, the controller may produce $RF_{Corrected}$ to compensate RF.

In one embodiment, the controller may determine $RF_{Corrected}$ using a resonance frequency (RF) correction model (e.g., retrieved from storage 44). In some embodiments, the model may be device specific, such that the controller retrieves the model using one or more characteristics, such as an identifier, of the ultrasonic instrument to retrieve the model. In which case, the controller may perform a table lookup into a data structure that associates RF correction models with characteristics, using the identifier to select a corresponding RF model. In some embodiments, the controller may use the model to determine an adjusted resonance frequency, $RF_{Adjusted}$, as output of the model in response to I as input into the model. In one embodiment, the model may be a (e.g., first-order) polynomial model that outputs $RF_{Adjusted}$ in response to I. In another embodiment, the RF correction model may be any type of model. The controller determines $RF_{Corrected}$ by adding $RF_{Adjusted}$ to RF, such that $RF_{Corrected}=RF+RF_{Adjusted}$. The controller determines a change in the cooling start resonance frequency, $\Delta RF_{CS}$, based on the RF Corrected (at block 74). In particular, the controller may determine $\Delta RF_{CS}$ based on a difference between $RF_{Corrected}$ and $RF_{CS}$, such as $\Delta RF_{CS}=RF_{Corrected}-RF_{CS}$.

The controller 40 determines whether the end effector is in contact with an object (at decision block 75). For example, the controller may determine whether the end effector is in contact with an object or is in-air based on whether I is greater than an impedance threshold, as described herein. If so, the controller 40 determines one or more model coefficients for a contact-cooling temperature model (at block 76). In particular, the controller may determine the model coefficients and/or the contact-cooling temperature model that may be used by the controller to estimate the temperature of the end effector, while it is touching an object and is in a cooling state. In one embodiment, the controller may determine the coefficients and the model, as described herein (e.g., based on characteristics of the ultrasonic instrument), and may retrieve the coefficients and model from storage 44.

In one embodiment, the controller may determine the model coefficients using $RF_{CS}$. For instance, the controller may perform a table lookup into the model coefficients 46 using $RF_{CS}$ to select one or more coefficients that may be associated with the cooling start resonance frequency.

In one embodiment, the temperature model used while the end effector is in contact with an object may be different than a temperature model used while the end effector is in-air. For example, when a hot object is in contact with a cooler object, heat is transferred (e.g., via conduction) from the hot object to the cooler object. In one embodiment, the rate at which conduction cools an object, such as the end effector 23, may be faster than when the end effector is air-cooled. As a result, the contact-cooling temperature model may be configured to account for a faster rate of cooling than an air-cooling temperature model, which may be used by the system 1 when the end effector is in air. In one embodiment, to account for the rate, the contact-cooling temperature model may be an exponential model, whereas an air-cooling temperature model may be a (e.g., second-order) polynomial model, where both models output a change in temperature, ΔT, in response to input, which may include one or more model coefficients and/or $RF_{CS}$, as described herein. In one embodiment, the exponential model may output a higher ΔT than the polynomial model with respect to the same input. This may be because the end effector may cool faster (e.g., dropping to a threshold temperature less than a period of time) when transferring heat due to conduction when in contact with another object, whereas the end effector may not cool as fast (e.g., the time to drop to the threshold temperature being greater than the period of time) when transferring heat into the air due to convection. In another embodiment, both models may be the same type of model. For example, both models may be polynomial models, but of different orders, such as the contact-cooling model being a third-order polynomial (e.g., cubic) model, whereas the air-cooling model may be a second-order polynomial model.

The controller 40 determines a change in temperature, ΔT, using the contact-cooling temperature model based on the (change in the) cooling start resonance frequency, $\Delta RF_{CS}$, and the model coefficients (at block 77). For instance, the controller may input $\Delta RF_{CS}$, and model coefficients into the exponential model, such as:

$$\Delta T = a*e^{b*\Delta RFCS} + c*e^{d*\Delta RFCS}$$

where e may be an exponential constant (e.g., Eulers number) and a, b, c, and d may be model coefficients. In another embodiment, the exponential model may be different with a different number of model coefficients. The controller 40 determines the temperature, T, of the end effector based on the starting temperature and the change in temperature (at block 78). In particular, T may be the combination of $T_{Start}$ and ΔT, such that $T=T_{Start}+\Delta T$. The controller 40 presents a notification based on the determined temperature of the end effector (at block 67).

Returning to decision block 75, if the end effector is not in contact with the object, the controller determines model coefficients for an air-cooling temperature model (at block 79). In one embodiment, the controller 40 may determine the model coefficients based on the air-cooling temperature model. As described herein, the air-cooling temperature model may be a second order polynomial model. In which case, the model may include three model coefficients a, b, and c. In one embodiment, the controller may determine the model coefficients based on $RF_{CS}$. For instance, each of the model coefficients may be based on functions of resonance frequency, f, such as $$a = f_a(RF_{CS})$$

$$b = f_b(RF_{CS})$$

$$c = f_c(RF_{CS})$$

where each of the coefficients may be determined by applying $RF_{CS}$ to a corresponding resonance frequency function. In one embodiment, to determine the model coefficients, the controller may determine their corresponding functions, $f_a$, $f_b$, and $f_c$. For instance, the controller may determine at least some of the functions based on one or more characteristics, such as an identifier of the ultrasonic instrument. In particular, the functions may be device-specific, such that the functions may change between different ultrasonic instruments. As a result, the controller may select the functions using characteristics, such as an identifier, of the ultrasonic instrument (e.g., by performing a table lookup into a data structure that stores functions associated with characteristics). In another embodiment, the model coefficients 46 stored in memory may include coefficients for different devices. As a result, the controller may determine the coefficients by performing a table lookup into the data structure that stores the model coefficients 46 in the storage using $RF_{CS}$ and one or more characteristics of the device.

The controller 40 determines $\Delta T$ using the air-cooling temperature model based on the (change in the) cooling start resonance frequency and the model coefficients (at block 81). For instance, the controller may determine $\Delta T$ as output of a (e.g., second-order) polynomial (e.g., quadradic) model based on input of $\Delta RF_{CS}$, and based on the determined polynomial model coefficients, such as:

$$\Delta T = a * \Delta RF_{CS}^2 + b * \Delta RF_{CS} + c$$

The controller 40 determines the temperature, T, of the end effector based on the starting temperature and the change in temperature (at block 78). In particular, T may be the combination of $T_{Start}$ and $\Delta T$, such that $T = T_{Start} + \Delta T$. The controller 40 presents a notification based on the determined temperature of the end effector (at block 67).

In one embodiment, the process 70 of FIG. 7 includes operations for estimating a temperature of an end effector of an ultrasonic instrument. This process may be performed using data that may be (e.g., dynamically) collected by the ultrasonic instrument, such as a resonance frequency. In another embodiment, the system 1 may be configured to estimate the temperature using one or more starting conditions and/or one or more ending conditions of the system 1. In which case, the system may estimate the temperature for any particular device and without needing to collect data from the ultrasonic instrument. FIG. 8 describes a process in which the temperature may be estimated using such conditions.

Turning to FIG. 8, this figure shows a flowchart of another embodiment of a process 80 for estimating a temperature of an end effector 23 of an ultrasonic instrument 20 while the end effector is in a cooling state. In particular, the process 80 include operations to estimate a temperature of the end effector based on baseline characteristics (or starting conditions) of the end effector. In one embodiment, baseline characteristics may be characteristics that are unique to a particular type of ultrasonic instrument. In another embodiment, the baseline characteristics may be determined while the ultrasonic instrument is at a starting condition, such as after a period of time of being activated (or plugged into a power supply). More about baseline characteristics is described herein.

The process 80 begins by the controller determining a baseline resonance frequency, $RF_{Baseline}$, of the end effector (e.g., blade) of the ultrasonic instrument (at block 81). In one embodiment, $RF_{Baseline}$ may be determined at an initial time, $t_0$, such as when the ultrasonic instrument 20 is coupled (e.g., plugged into) the generator 25. For instance, once the instrument is plugged into the generator, the controller may perform one or more diagnostic operations upon the instrument (e.g., to determine one or more characteristics, as described herein) to determine $RF_{Baseline}$. In another embodiment, the generator may be configured to determine $RF_{Baseline}$, and provide the frequency to the controller 40. Thus, based on the operations, the generator may determine the baseline frequency of the end effector's blade, and provide the frequency to the controller.

In some embodiments, this baseline resonance frequency may be determined while the end effector is at (or approximately) room temperature (e.g., a temperature between 20-25° C.) and/or while the end effector is in air (e.g., while the blade of the end effector is not touching an object). In another embodiment, the baseline resonance frequency may be determined once and stored in the storage 44 (or memory of the controller 40 of) the surgical system 1. For instance, the baseline frequency may be determined a first time the instrument is coupled to the generator, may be stored in storage 44, and retrieved by the controller when necessary. In another embodiment, the baseline frequency may be determined every time the ultrasonic instrument is plugged into the generator. In another embodiment, the baseline frequency may be determined at start up (e.g., during initial powering up) of the (e.g., ultrasonic instrument by the) surgical system. In another embodiment, the baseline frequency may be a resonance frequency that was previously determined (e.g., during a previous performance of the process 80).

In one embodiment, the $RF_{Baseline}$ may be determined while the ultrasonic instrument is in the low-power state, the end effector is in an open position, and/or the (e.g., end effector and shaft of the) ultrasonic instrument is not in contact with any objects. In another embodiment, the $RF_{Baseline}$ may be determined when (e.g., every time) the ultrasonic instrument enters a cooling cycle.

The controller 40 determines a baseline temperature, $T_{Baseline}$, of the end effector (at block 82). In one embodiment, the baseline temperature may be at (or approximately) room temperature. In another embodiment, $T_{Baseline}$ may be a temperature measured by a temperature sensor of the surgical system. For instance, $T_{Baseline}$ may be a temperature of the end effector after a period of time within an environment. In another embodiment, $T_{Baseline}$ may be a temperature of the end effector that is measured after the end effector has been in the cooling state for a period of time. In some embodiments, $T_{Baseline}$ may be a predefined temperature.

In one embodiment, the operations described in block 81 and/or 82 may be performed at any time. In particular, the operations may be performed prior to the ultrasonic instrument entering a current cooling state.

The controller 40 determines the starting temperature, $T_{Start}$, of the end effector of the ultrasonic instrument (at block 61). The controller 40 determines the cooling start resonance frequency, $RF_{CS}$, of the end effector (at block 71). The controller 40 determines a resonance frequency, RF, of the end effector (at block 63), and determines the impedance, I, of the end effector (at block 72). The controller 40 determines the corrected resonance frequency, $RF_{Corrected}$, based on I and RF, as described herein (at block 73). The controller determines whether the end effector is in contact with an object (at decision block 75).

Responsive to determining that the end effector is not in contact with an object (e.g., is in-air), the controller 40 determines model coefficients for an in-air cooling temperature model based on the $T_{Start}$, $RF_{CS}$, $RF_{Baseline}$, and/or $T_{Baseline}$ (at block 85). As described herein, the temperature of the end effector may follow a polynomial curve, such that the temperature may be defined as the following polynomial function:

$$T = a * RF^2 + b * RF + c$$

In which case, the model coefficients may be determined based on initial conditions and end conditions of the end effector. In particular, the initial condition may be the starting temperature with respect to the cooling start resonance frequency, which may be defined as:

$$T_{Start} = a * RF_{CS}^2 + b * RF_{CS} + c$$

An end condition may include baseline conditions of the end effector (e.g., when the end effector is cooled to a threshold temperature, such as room temperature) may be the baseline temperature with respect to the baseline resonance frequency, which may be defined as:

$$T_{Baseline} = a * RF_{Baseline}^2 + b * RF_{Baseline} + c$$

In addition, since the model is a second-order polynomial, and the slope at the end of cooling may be equal to zero, as an end condition, a derivative of the $T_{Baseline}$ function may be taken, resulting in a first-order polynomial such as:

$$0 = 2 * a * RF_{Baseline} + b$$

In particular, the derivative of the model may be zero due to it converging to the baseline temperature (e.g., which may be converge asymptotically). Knowing the initial and end conditions, the polynomial equations may be added to a 3×3 polynomial matrix that is multiplied by a model coefficient matrix (extracted from the polynomial equations) to equal a temperature matrix, as follows:

$$\begin{bmatrix} T_{Start} \\ T_{Baseline} \\ 0 \end{bmatrix} = \begin{bmatrix} RF_{CS}^2 & RF_{CS} & 1 \\ RF_{Baseline}^2 & RF_{Baseline} & 1 \\ 2 * RF_{Baseline} & 1 & 0 \end{bmatrix} * \begin{bmatrix} a \\ b \\ c \end{bmatrix}$$

Since the starting and baseline temperatures, and the starting and baseline resonance frequencies are known, the controller 40 may solve for each of the model coefficients according to the matrix equation. In particular, the model coefficients of the coefficient matrix may be determined by multiplying each side by the inverse 3×3 polynomial matrix. In one embodiment, the controller may determine the model coefficients by performing a table lookup into the model coefficient's 46 data structure using the known temperatures and resonance frequencies. In one embodiment, the model coefficients determined based on the initial and end conditions may be device specific. In another embodiment, the coefficients may not be device specific.

The controller 40 determines a temperature using the air-cooling temperature model based on the (corrected) resonance frequency and the determined model coefficients (at block 86). In particular, the (e.g., current) temperature, T, of the end effector may be defined as $$T = a * RF_{Corrected}^2 + b * \Delta RF_{Corrected} + c$$

where the model coefficients that are used may be determined according to the matrix equation using the initial and/or end conditions, as described herein. The controller presents a notification based on the temperature of the end effector (at block 67).

Returning to decision block 75, if the end effector is in contact with an object, the controller 40 determines model coefficients for a contact-cooling temperature model based on $T_{Start}$, $RF_{CS}$, $RF_{Baseline}$, and/or $T_{Baseline}$ (at block 83). As described herein, since the temperature of the end effector may decrease more rapidly while in contact with an object, as opposed to while in-air, the contact-cooling temperature model may account for the speed at which the end effector cools. As a result, the temperature of the end effector may follow a third-order polynomial curve, such that the temperature of the end effector may be defined as the following function:

$$T = a * RF^3 + b * RF^2 + c * RF + d$$

where the contact-cooling model may include four coefficients, a, b, c, and d. In which case, the model coefficients may be determined based on initial conditions and end conditions of the end effector. In particular, the initial conditions may be the starting temperature with respect to the cooling start resonance frequency, which may be defined as:

$$T_{Start} = a * RF_{CS}^3 + b * RF_{CS}^2 + c * RF_{CS} + d$$

An end condition may be a baseline conditions that may be defined as:

$$T_{Baseline} = a * RF^3_{Baseline} + b * RF^2_{Baseline} + c * RF_{Baseline} + d$$

Also, since the slope at the end of cooling may be equal to zero, as end conditions, a first and second derivative of $T_{Baseline}$ may be taken, resulting in the following:

$$0 = 3 * a * RF^2_{Baseline} + 2 * b * RF_{Baseline} + 1$$

and $$0 = 6 * a * RF_{Baseline} + 2 * b$$

Knowing the initial and end conditions, the polynomial equations may be added to a polynomial matrix that is multiplied by a model coefficient matrix to equal a temperature matrix, as follows:

$$\begin{bmatrix} T_{Start} \\ T_{Baseline} \\ 0 \\ 0 \end{bmatrix} = \begin{bmatrix} RF^3_{CS} & RF^2_{CS} & RF_{CS} & 1 \\ RF^3_{Baseline} & RF^2_{Baseline} & RF_{Baseline} & 1 \\ 3 * RF^2_{Baseline} & 2 * RF_{Baseline} & 1 & 0 \\ 6 * RF_{Baseline} & 2 & 0 & 0 \end{bmatrix} * \begin{bmatrix} a \\ b \\ c \\ d \end{bmatrix}$$

The controller 40 may be configured to solve for each of the four model coefficients by multiplying each side of the matrix equation with the inverse 4×4 polynomial matrix, as described herein. The controller 40 determines a temperature using the contact cooling temperature model based on the (corrected) resonance frequency and the determined four model coefficients (at block 84). In particular, the temperature, T, of the end effector may be defined as:

$$T = a * RF^3_{Corrected} + b * RF^2_{Corrected} + c * RF_{Corrected} + d$$

Where the model coefficients, a, b, c, and d that are used may be determined according to the matrix equation, as described herein. The controller 40 than may present a notification based on the temperature of the end effector at block 67.

Some embodiments may perform variations to at least some of the processes described herein. For example, the specific operations of at least some of the processes may not be performed in the exact order shown and described. The specific operations may not be performed in one continuous series of operations and different specific operations may be performed in different embodiments. For example, the operations within dashed boxes may be optional operations, such as operations at blocks 63, 72, 73, and/or 74 in process 70. In the case in which these operations are not performed, when determining the temperature using the air-cooling temperature model, at block 81, the cooling start resonance frequency determined at block 71 and the determined model coefficients may be used as input into the model which may produce the temperature as output. Otherwise, when the operations at 63, 72, 73 and/or 74 are performed, a change in the cooling start resonance frequency determined at block 74 may be used (e.g., as input into the air-cooling temperature model) to estimate the temperature.

Figure 9:
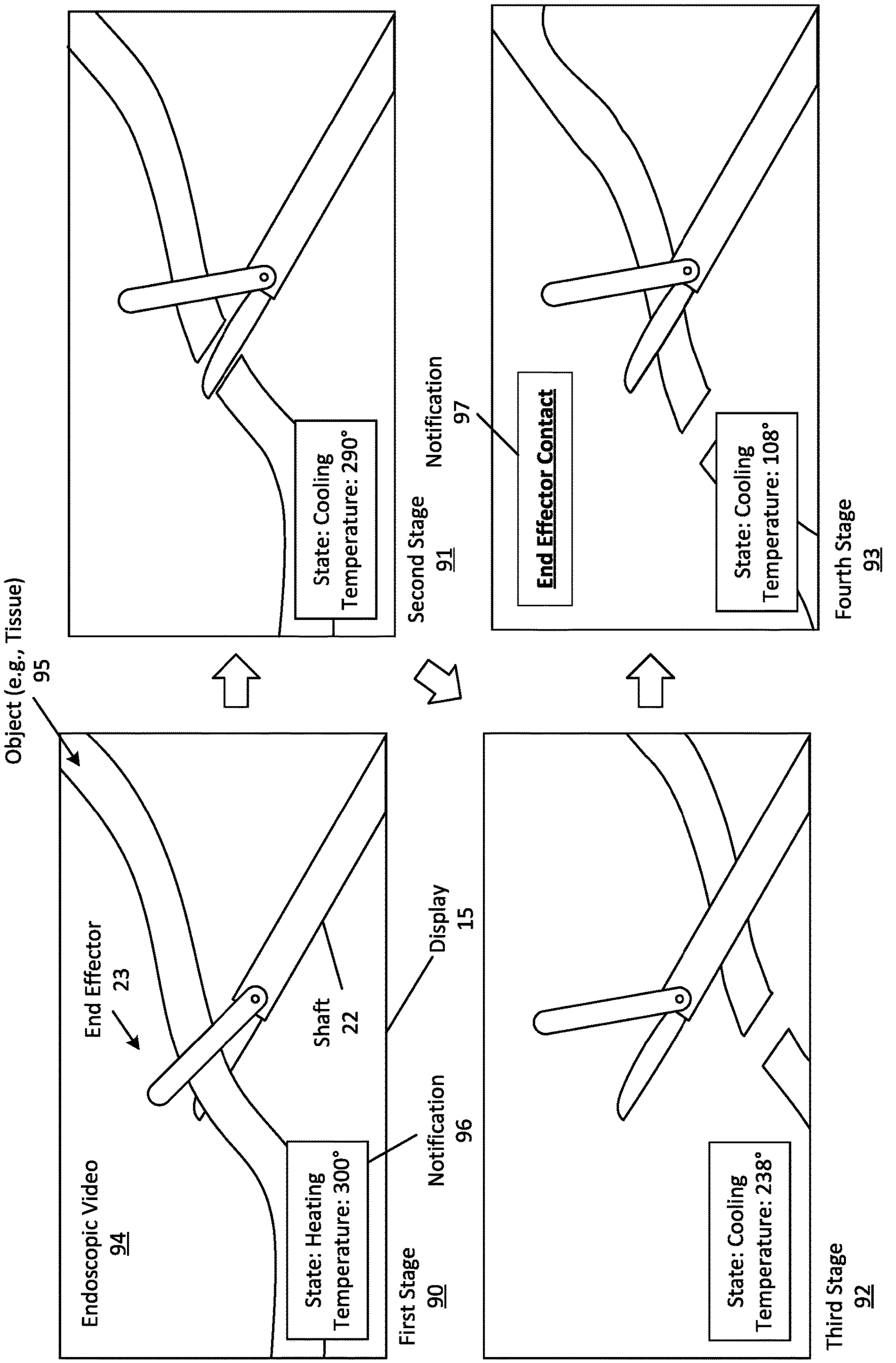
FIG. 9 show several stages of a display of the surgical system that is showing actions performed by the end effector of the ultrasonic instrument, and is showing a temperature of the end effector.

FIG. 9 show several stages of a display of the surgical system that is showing actions performed by the end effector of the ultrasonic instrument and is showing a temperature of the end effector. Specifically, each of the four stages 90-93 is showing a display 15, which is displaying an endoscopic video 94 (captured by an endoscope, during a surgical procedure) that is showing an end effector 23 and a shaft 22 of the ultrasonic instrument, and a portion of an object 95 (e.g., a tissue, such as a blood vessel), at a surgical site (e.g., within an abdomen of a patient). Each of the stages also shows a notification 96 that is superimposed (overlaid) on top of a portion of the endoscopic video 94. The notification 96 includes information regarding the state and the temperature of the end effector. In one embodiment, the state and/or the temperature may be determined by the surgical system according to at least some of the temperature estimation operations described herein. In one embodiment, the display showing the endoscopic video may be a different display of the surgical system, such as display 24 of the generator 25. In some embodiments, the display may show other content, such as other video content and/or a graphical user interface (GUI) of the surgical system that is displaying one or more UI items (e.g., associated with a surgical procedure that is being performed by an operator of the system).

The first stage 90 shows that the end effector is grasping a portion of the tissue in order to cut the tissue. At this stage, the ultrasonic instrument may be in or entering the heating cycle, due to the hinged arm 31 being in a closed position, thereby squeezing the tissue between the arm 31 and the blade. Thus, as described herein, while in the closed position and in the heating cycle, the blade may cut the tissue using frictional heat due to oscillations of the blade.

In addition, the surgical system may be configured to perform temperature estimation operations to determine the state in which the end effector is operating and estimate the temperature of the end effector. In particular, the (e.g., controller 40 of the) surgical system 1 may perform at least some operations described herein to determine whether the ultrasonic instrument is in the heating cycle. For example, the system may determine whether the input current into the ultrasonic instrument is greater than (or equal to) an input current threshold, as described in process 50 of FIG. 5. Upon determining that the input current is greater than the threshold, the system may estimate the temperature using the heating model, as described in process 60 of FIG. 6. As shown, the system presents a (e.g., pop-up) notification 96 illustrating the result of estimating the temperature. Specifically, the notification 96 indicates that the state of the system is in a heating cycle and that the temperature is at 300°.

The second stage 91 shows the result of the end effector 23 cutting the tissue 95. In particular, this stage shows that the tissue has been cut into two pieces. In addition, the ultrasonic instrument is in the cooling cycle, with the hinged arm in the open position, and is in the air. Thus, at this stage the surgical system may be configured to determine that the ultrasonic instrument has transitioned from the heating state to the cooling state based on changes to one or more characteristics. For example, the system may determine that the input current has dropped below the input current threshold, as described in FIG. 5. In response, the system may estimate a temperature of the end effector based on a cooling model. Specifically, the system may determine based on characteristics, such as impedance of the end effector that the end effector 23 is in-air and may perform temperature estimation operations using an air-cooling temperature model, as described in FIG. 7 and/or FIG. 8. This stage shows the result of temperature estimation while the end effector is in air by changing the notification 96 to indicate that the state of the end effector is now cooling and the temperature is 290°.

The third stage 92 shows that the end effector 23 has been moved upward in order to allow the end effector to continue to cool in-air. In one embodiment, the surgical system may continue to perform temperature estimation operations in order to dynamically update the temperature of the end effector (in real-time). As a result, the notification 96 indicates that the temperature has dropped from 290° to 238°.

The fourth stage 93 shows that the blade 30 of the end effector 23 has moved and is now touching the tissue 95. This stage is also showing that a notification 97 is displayed on the display 15 that indicates "End Effector Contact", in order to notify the operator that the (blade of the) end effector is touching an object. As described herein, the surgical system 1 may be configured to determine whether the end effector is in contact with an object or is in-air based on an impedance of the end effector. In particular, upon determining that the impedance is greater than (or equal to) an impedance threshold, the surgical system may transition from estimating the temperature using an in-air cooling model (from the third stage 92) to estimating the temperature using a contact cooling model, as described in either (or both) of FIGS. 7 and 8. As a result of estimating the temperature, the notification 96 is updated to indicate that the temperature is now 108°.

Thus, this figure is illustrating how the controller 40 may (e.g., continuously) perform at least some of the operations of the processes described herein to continuously monitor and update the operator of the state and temperature of the instrument.

Figure 10:
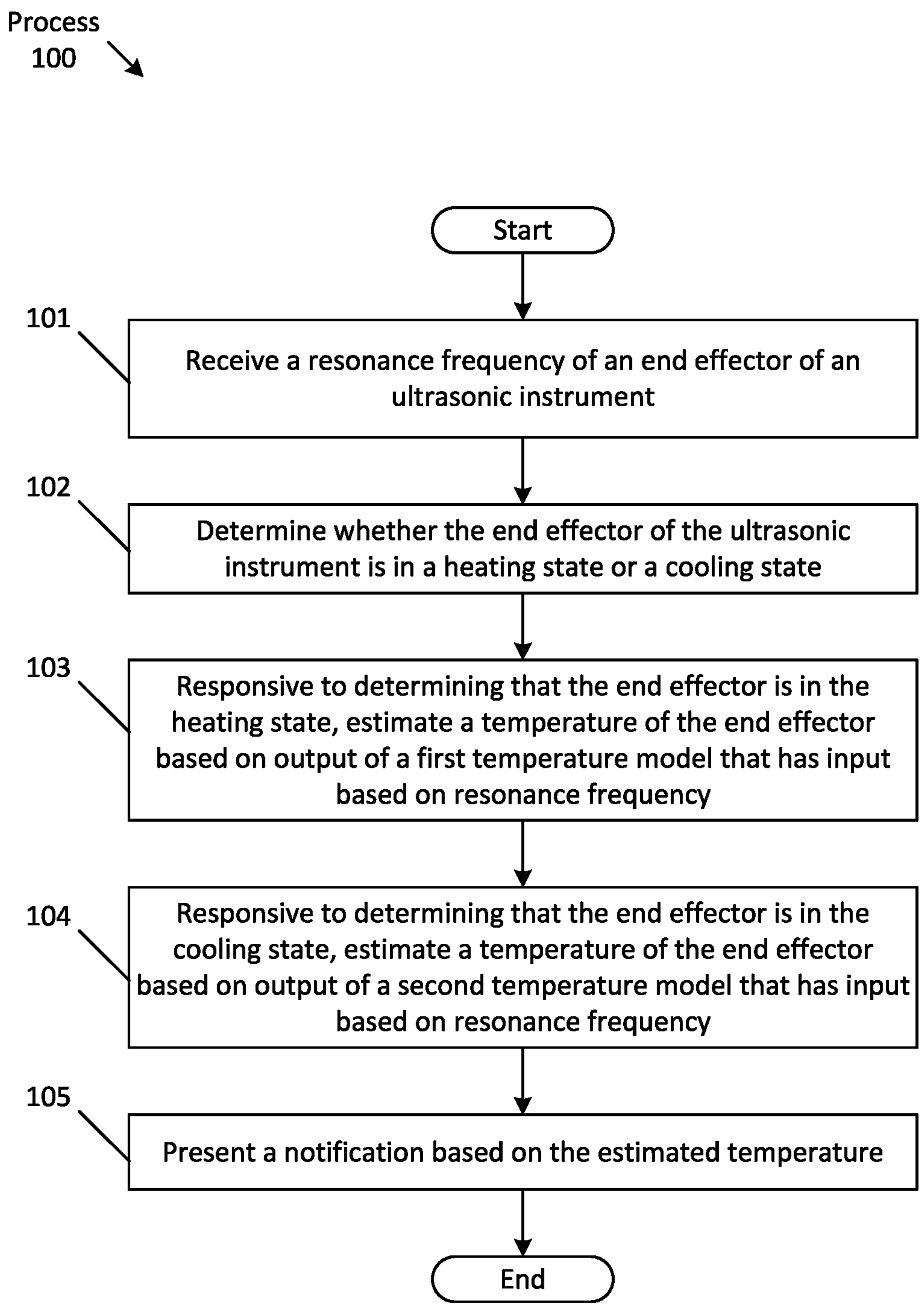
FIG. 10 is a flowchart of another embodiment of a process for estimating a temperature of an end effector of an ultrasonic instrument.

FIG. 10 is a flowchart of another embodiment of a process 100 for estimating a temperature of an end effector of an ultrasonic instrument. The process 100 begins by the controller 40 receiving a resonance frequency of the end effector of an ultrasonic instrument (at block 101). For example, the resonance frequency may be a starting resonance frequency. The controller determines whether the end effector of the ultrasonic instrument is in a heating state or a cooling state (at block 102). As described herein, the controller may determine which state the ultrasonic instrument is in based on one or more characteristics, such as input current and/or impedance of the instrument. Responsive to determining that the end effector is in the heating state, the controller estimates a temperature of the end effector based on output of a first temperature model (e.g., the heating model, described herein) that has input based on the resonance frequency of the end effector (at block 103). Responsive, however, to determining that the end effector is in the cooling state, the controller estimates a temperature of the end effector based on output of a second temperature model (e.g., an in-air cooling model or a contact-cooling model) that has input based on the resonance frequency (at block 104). In one embodiment, the temperature may be determined by applying input into the second temperature model based on a second (or subsequent) resonance frequency of the end effector and one or more model coefficients. For example, the controller may determine a change a corrected resonance frequency based on the subsequent resonance frequency and may apply the corrected frequency and the model coefficients as input into the model to estimate the temperature, as output of the model. The controller presents a notification based on the estimated temperature (at block 105).

Some embodiments may perform variations to at least some of the processes described herein. For example, the specific operations of at least some of the processes may not be performed in the exact order shown and described. The specific operations may not be performed in one continuous series of operations and different specific operations may be performed in different embodiments. For example, the operations within dashed boxes may be optional operations that may not be performed while (or each time) a respective process is performed. In another embodiment, one or more operations that have solid boundary boxes may be optional. In one embodiment, at least some of the operations described herein (e.g., performed in one or more processes described herein) may be performed automatically (e.g., without user interference). For example, at least some operations may be performed at any stage during a surgical procedure in which an ultrasonic instrument is being used by an operator. In some embodiments, at least some of the operations described herein may be performed (e.g., continuously) in real-time (e.g., while the ultrasonic is used during a surgical procedure), and/or at least some operations may be performed prior to use during a surgical procedure.

As described herein, the surgical system 1 may be configured to perform temperature estimation operations based on one or more determined characteristics of the ultrasonic instrument, such as resonance frequency. In one embodiment, the characteristics used by the surgical system may be averages over a period of time. For example, the second resonance frequency, RF, determined at block 63 of process 60 in FIG. 6 may be an average resonance frequency over a period of time (e.g., ten seconds).

As described herein, the controller may estimate and display the temperature of the end effector. In one embodiment, the temperature of the end effector (or an indication of the temperature) may be displayed as a separate notification than (or in the same) a notification that indicates the state of the end effector. In another embodiment, the notification presented by the controller may include other information, such as whether the end effector is in contact with an object or is in-air.

In some embodiments, the controller may update the baseline resonance frequency and/or baseline temperature when the ultrasonic instrument switches from a heating cycle into a cooling cycle, and/or vice versa. In particular, the controller may determine that the ultrasonic instrument is in a heating cycle (e.g., the end effector being in a closed position), and in response to determining that the ultrasonic instrument has returned to the cooling cycle (e.g., the end effector now being in the open position and/or in air), the controller may (e.g., begin) to monitor the resonance frequency of the end effector over the period of time to determine a new baseline resonance frequency.

As previously explained, an embodiment of the disclosure may be a non-transitory machine-readable medium (such as microelectronic memory) having stored thereon instructions, which program one or more data processing components (generically referred to here as a "processor") to (automatically) perform ultrasonic instrument operations and/or temperature estimation operations, as described herein. In other embodiments, some of these operations might be performed by specific hardware components that contain hardwired logic. Those operations might alternatively be performed by any combination of programmed data processing components and fixed hardwired circuit components.

To aid the Patent Office and any readers of any patent issued on this application in interpreting the claims appended hereto, applicants wish to note that they do not intend any of the appended claims or claim elements to invoke 35 U.S.C. 112(f) unless the words “means for” or “step for” are explicitly used in the particular claim.

While certain embodiments have been described and shown in the accompanying drawings, it is to be understood that such embodiments are merely illustrative of and not restrictive on the broad disclosure, and that the disclosure is not limited to the specific constructions and arrangements shown and described, since various other modifications may occur to those of ordinary skill in the art. The description is thus to be regarded as illustrative instead of limiting.

In some embodiments, this disclosure may include the language, for example, “at least one of [element A] and [element B].” This language may refer to one or more of the elements. For example, “at least one of A and B” may refer to “A,” “B,” or “A and B.” Specifically, “at least one of A and B” may refer to “at least one of A and at least one of B,” or “at least of either A or B.” In some embodiments, this disclosure may include the language, for example, “[element A], [element B], and/or [element C].” This language may refer to either of the elements or any combination thereof. For instance, “A, B, and/or C” may refer to “A,” “B,” “C,” “A and B,” “A and C,” “B and C,” or “A, B, and C.”

What is claimed is:

1. A method comprising:

determining a resonance frequency of an end effector of an ultrasonic instrument;

determining whether the end effector of the ultrasonic instrument is in a heating state in which at least one of an input current, an input voltage, or an excursion of the end effector is to cause the ultrasonic instrument to generate heat for performing a surgical task or a cooling state in which the at least one of the input current, the input voltage, or the excursion of the end effector is to cause the ultrasonic instrument to generate less heat than in the heating state or no heat;

responsive to determining that the end effector is in the heating state, estimating a temperature of the end effector based on output of a first temperature model that has input based on the resonance frequency;

responsive to determining that the end effector is in the cooling state, estimating the temperature of the end effector based on output of a second temperature model that has input based on the resonance frequency; and presenting a notification based on the temperature.

2. The method of claim 1, wherein the resonance frequency is a first resonance frequency that is at a starting time at which the end effector enters the heating state or the cooling state, wherein the method further comprises:

determining a starting temperature of the end effector at the starting time; and determining a second resonance frequency of the end effector of the ultrasonic instrument at a time that is subsequent to the starting time, wherein the temperature is estimated based on the starting temperature, the first resonance frequency, and the second resonance frequency.

3. The method of claim 2, wherein estimating the temperature, responsive to determining that the end effector is in the heating state, comprises:

determining a change in temperature of the end effector based on a difference between the first resonance frequency and the second resonance frequency; and combining the change in temperature and the starting temperature.

4. The method of claim 1, wherein estimating the temperature, responsive to determining that the end effector is in the cooling state, comprises:

determining whether the end effector is being air-cooled or is being contact-cooled;

responsive to determining that the end effector is being air-cooled, estimating the temperature of the end effector based on output of a first cooling temperature model; and responsive to determining that the end effector is being contact-cooled, estimating the temperature of the end effector based on output of a second cooling temperature model.

5. The method of claim 4, wherein the first cooling temperature model is a polynomial model, and the second cooling temperature model is an exponential model.

6. The method of claim 1, wherein the resonance frequency is a first resonance frequency, wherein estimating the temperature of the end effector based on output of the second temperature model comprises:

determining model coefficients for the second temperature model based on the first resonance frequency;

determining a second resonance frequency of the end effector of the ultrasonic instrument; and determining the temperature by applying input into the second temperature model based on the second resonance frequency and the model coefficients.

7. The method of claim 6 further comprising:

determining an impedance of the end effector based on the input current of the ultrasonic instrument; and determining a corrected resonance frequency based on the impedance and the second resonance frequency, wherein determining the temperature of the end effector based on output of the second temperature model comprises applying the corrected resonance frequency as input into the second temperature model.

8. The method of claim 1 further comprising determining the input current that is being provided to the ultrasonic instrument, wherein determining whether the end effector is in a heating state or a cooling state comprises:

determining that the end effector is in the heating state when the input current is greater than a current threshold; and determining that the end effector is in the cooling state when the input current is less than the current threshold.

9. The method of claim 8 further comprising:

determining an impedance of the end effector based on the input current;

responsive to determining that the impedance is less than a threshold, determining that the end effector is in the cooling state while in-air; and responsive to determining that the impedance is greater than the threshold, determining that the end effector is in the cooling state while in contact with an object.

10. A surgical system comprising:

an ultrasonic instrument with an end effector;

a display;

a processor; and memory having instructions which when executed by the processor causes the surgical system to:

determine a resonance frequency of the end effector;

determine whether the end effector is in a heating state in which at least one of an input current, an input voltage, or an excursion of the end effector is to cause the ultrasonic instrument to generate heat for performing a surgical task or a cooling state in which at least one of the input current, the input voltage, or the excursion of the end effector is to cause the ultrasonic instrument to generate less heat than in the heating state or no heat;

responsive to determining that the end effector is in the heating state, estimate a temperature of the end effector based on output of a first temperature model that has input based on the resonance frequency;

responsive to determining that the end effector is in the cooling state, estimate the temperature of the end effector based on output of a second temperature model that has input based on the resonance frequency; and display a notification that includes the temperature on the display.

11. The surgical system of claim 10, wherein the resonance frequency is a first resonance frequency that is at a starting time at which the end effector enters the heating state or the cooling state, wherein the memory has further instructions to:

determine a starting temperature of the end effector at the starting time; and determine a second resonance frequency of the end effector at a time that is subsequent to the starting time, wherein the temperature is estimated based on the starting temperature, the first resonance frequency, and the second resonance frequency.

12. The surgical system of claim 11, wherein instructions to estimate the temperature, responsive to determining that the end effector is in the heating state, comprises instructions to:

determine a change in temperature of the end effector based on a difference between the first resonance frequency and the second resonance frequency; and combine the change in temperature and the starting temperature.

13. The surgical system of claim 10, wherein the instructions to estimate the temperature, responsive to determining that the end effector is in the cooling state, comprises instructions to:

determine whether the end effector is being air-cooled or is being contact-cooled;

responsive to determining that the end effector is being air-cooled, estimate the temperature of the end effector based on output of a first cooling temperature model; and responsive to determining that the end effector is being contact-cooled, estimate the temperature of the end effector based on output of a second cooling temperature model, wherein the first cooling temperature model is a polynomial model, and the second cooling temperature model is an exponential model.

14. The surgical system of claim 10, wherein the resonance frequency is a first resonance frequency, wherein instructions to estimate the temperature of the end effector based on output of the second temperature model comprises instructions to:

determine model coefficients for the second temperature model based on the first resonance frequency;

determine a second resonance frequency of the end effector of the ultrasonic instrument; and determine the temperature by applying input into the second temperature model based on the second resonance frequency and the model coefficients.

15. The surgical system of claim 14, wherein the memory has further instructions to:

determine an impedance of the end effector based on the input current of the ultrasonic instrument; and determine a corrected resonance frequency based on the impedance and the second resonance frequency, wherein the instructions to determine the temperature of the end effector based on output of the second temperature model comprises instructions to apply the corrected resonance frequency as input into the second temperature model.

16. A non-transitory machine-readable medium comprising instructions which when executed by at least one processor of a surgical system causes the surgical system to:

determine a resonance frequency of an end effector of an ultrasonic instrument;

determine whether the end effector of the ultrasonic instrument is in a heating state in which at least one of an input current, an input voltage, or an excursion of the end effector is to cause the ultrasonic instrument to generate heat for performing a surgical task or a cooling state in which at least one of the input current, the input voltage, or the excursion of the end effector is to cause the ultrasonic instrument to generate less heat than in the heating state or no heat;

responsive to determining that the end effector is in the heating state, estimate a temperature of the end effector based on output of a first temperature model that has input based on the resonance frequency;

responsive to determining that the end effector is in the cooling state, estimate the temperature of the end effector based on output of a second temperature model that has input based on the resonance frequency; and present a notification based on the temperature.

17. The non-transitory machine-readable medium of claim 16, wherein the resonance frequency is a first resonance frequency that is at a starting time at which the end effector enters the heating state or the cooling state, wherein the non-transitory machine-readable medium has further instructions to:

determine a starting temperature of the end effector at the starting time; and determine a second resonance frequency of the end effector of the ultrasonic instrument at a time that is subsequent to the starting time, wherein the temperature is estimated based on the starting temperature, the first resonance frequency, and the second resonance frequency.

18. The non-transitory machine-readable medium of claim 17, wherein the instructions to estimate the temperature, responsive to determining that the end effector is in the heating state, comprises instructions to:

determine a change in temperature of the end effector based on a difference between the first resonance frequency and the second resonance frequency; and combine the change in temperature and the starting temperature.

19. The non-transitory machine-readable medium of claim 16, wherein the instructions to estimate the temperature, responsive to determining that the end effector is in the cooling state, comprises instructions to:

determine whether the end effector is being air-cooled or is being contact-cooled;

responsive to determining that the end effector is being air-cooled, estimate the temperature of the end effector based on output of a first cooling temperature model; and responsive to determining that the end effector is being contact-cooled, estimate the temperature of the end effector based on output of a second cooling temperature model.

20. The non-transitory machine-readable medium of claim 16, wherein the resonance frequency is a first resonance frequency, wherein the instructions to estimate the temperature of the end effector based on output of the second temperature model comprises instructions to:

determine model coefficients for the second temperature model based on the first resonance frequency;

determine a second resonance frequency of the end effector of the ultrasonic instrument; and determine the temperature by applying input into the second temperature model based on the second resonance frequency and the model coefficients.

* * * * *